US010881688B2

(12) United States Patent
Leek et al.

(10) Patent No.: US 10,881,688 B2
(45) Date of Patent: Jan. 5, 2021

(54) MODIFIED GAMMA DELTA T CELLS AND USES THEREOF

(71) Applicant: TC BIOPHARM LTD, Penicuik Lothian (GB)

(72) Inventors: Michael David Leek, Edinburgh Lothian (GB); Adele Hannigan, Glasgow Strathclyde (GB); Agapitos Patakas, Glasgow Strathclyde (GB); Daria Paruzina, Edinburgh Lothian (GB)

(73) Assignee: TC BIOPHARM LTD, Penicuik Lothian (GB)

( * ) Notice: Subject to any disclaimer, the term of this patent is extended or adjusted under 35 U.S.C. 154(b) by 176 days.

(21) Appl. No.: 15/566,324

(22) PCT Filed: Apr. 14, 2016

(86) PCT No.: PCT/GB2016/051050
§ 371 (c)(1),
(2) Date: Oct. 13, 2017

(87) PCT Pub. No.: WO2016/166544
PCT Pub. Date: Oct. 20, 2016

(65) Prior Publication Data
US 2018/0125889 A1    May 10, 2018

(30) Foreign Application Priority Data

Apr. 15, 2015  (GB) .................................. 1506423.1
Jul. 8, 2015   (WO) ................ PCT/GB2015/051985

(51) Int. Cl.
*A61K 35/17* (2015.01)
*C07K 14/725* (2006.01)
*C12N 5/0783* (2010.01)
*A61K 31/00* (2006.01)

(52) U.S. Cl.
CPC .............. *A61K 35/17* (2013.01); *A61K 31/00* (2013.01); *C07K 14/7051* (2013.01); *C12N 5/0638* (2013.01); *C07K 2317/53* (2013.01); *C07K 2317/732* (2013.01); *C07K 2317/92* (2013.01); *C07K 2319/00* (2013.01); *C07K 2319/02* (2013.01); *C07K 2319/03* (2013.01); *C12N 2501/2302* (2013.01); *C12N 2510/00* (2013.01)

(58) Field of Classification Search
CPC ..................................................... A61K 35/17
See application file for complete search history.

(56) References Cited

U.S. PATENT DOCUMENTS 9,907,820 B2      3/2018  Cooper et al.
2014/0099309 A1   4/2014  Powell, Jr. et al.
2015/0038684 A1   2/2015  Jensen
2016/0175358 A1   6/2016  Jakobovits et al.
2018/0125890 A1   5/2018  Anderson et al.

FOREIGN PATENT DOCUMENTS

| IL | 247208 B | 2/2020 |
|---|---|---|
| IL | 272264 A | 2/2020 |
| JP | 2003-529363 A | 10/2002 |
| JP | 2002-535002 A | 10/2003 |
| JP | 2008-509683 A | 4/2008 |
| WO | WO 2008/152822 A1 | 12/2008 |
| WO | WO 2014/124143 A1 | 8/2014 |
| WO | WO 2014/186469 A2 | 11/2014 |
| WO | WO 2015/017214 A1 | 2/2015 |
| WO | WO 2015/066262 A1 | 5/2015 |
| WO | WO 2015/075468 A1 | 5/2015 |
| WO | WO 2015/123642 A1 | 8/2015 |
| WO | WO 2015/164594 A1 | 10/2015 |
| WO | WO 2016/005752 A1 | 1/2016 |
| WO | WO 2016/166544 A1 | 10/2016 |
| WO | WO 2016/174461 A1 | 11/2016 |

OTHER PUBLICATIONS

Pizzitola et al., "In Vitro Comparison of Three Different Chimeric Receptor-modified Effector T-cell Populations for Leukemia Cell Therapy," J Immunother, 34(6):469-479, (2011).
WIPO Application No. PCT/GB2015/051985, PCT International Preliminary Report on Patentability dated Jan. 10, 2017.
WIPO Application No. PCT/GB2016/051050, PCT International Preliminary Report on Patentability dated Oct. 19, 2017.
WIPO Application No. PCT/GB2016/051235, PCT International Preliminary Report on Patentability dated Oct. 31, 2017.
WIPO Application No. PCT/GB2016/051235, PCT International Search Report dated Jun. 29, 2016.
WIPO Application No. PCT/GB2016/051235, PCT Written Opinion of the International Searching Authority dated Jun. 29, 2016.
EP 16720532.7 European Examination Report dated Mar. 13, 2019.
"TCRγ/δ+ T Cell Isolation Kit: human," Order No. 130-092-892, Miltenyi Biotec GmBH, 3 pages, (2007).
Bonneville and Scotet, "Human Vγ9Vδ2 T cells: promising new leads for immunotherapy of infections and tumors," Current Opinion in Immunology, 18:539-546, (2006).

(Continued)

*Primary Examiner* — Thaian N. Ton
*Assistant Examiner* — David A. Montanari
(74) *Attorney, Agent, or Firm* — Alston & Bird LLP

(57) ABSTRACT

The present invention provides composition and methods for the treatment of cancer or infectious diseases in a human. The invention includes the generation and administration of gamma delta T cells that express chimeric antigen receptors (CARs) comprising an antigen binding domain, a hinge domain, a transmembrane domain, a costimulatory signalling domain with the inclusion or not of a CD3 zeta signalling domain. Expression of CAR sequence omitting the CD3 zeta signalling domain in gamma delta T cells, provides for a CAR-T therapy in vivo, which will effect cytolysis only on target cells providing ligands for activation of the gamma delta T cell receptor (TCR).

8 Claims, 13 Drawing Sheets

Figure 1:
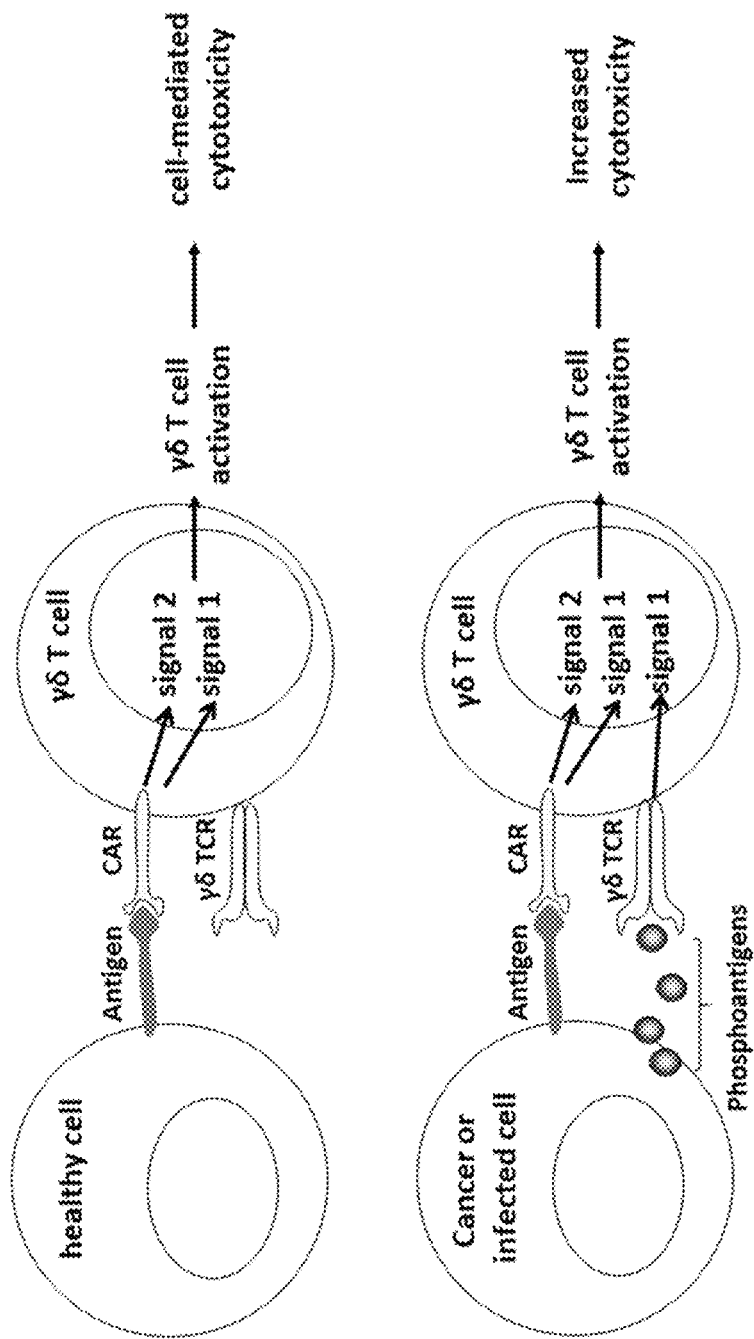

Specification includes a Sequence Listing.

(56) References Cited

OTHER PUBLICATIONS

Fedorov et al., "PD-1- and CTLA-4-Based Inhibitory Chimeric Antigen Receptors (iCARs) Divert Off-Target Immunotherapy Responses," Sci. Transl. Med., 5(215):215ra172, 25 pages, (2013).
Knight et al., "Human Vdeltal gamma-delta T cells exert potent specific cytotoxicity against primary multiple myeloma cells," Cytotherapy, 14:1110-1118, (2012).
Kowolik et al., "CD28 Costimulation Provided through a CD19-Specific Chimeric Antigen Receptor Enhances In vivo Persistence and Antitumor Efficacy of Adoptively Transferred T Cells," Cancer Res., 66(22):10995-11004, (2006).
Sadelain et al., "The Basic Principles of Chimeric Antigen Receptor Design," Cancer Discovery, 3(4):388-398, (2013).
Santolaria et al., "Repeated Systemic Administrations of Both Aminobisphosphonates and Human Vγ9δ32 T Cells Efficiently Control Tumor Development In Vivo," J. Immunol., 191:1993-2000, (2013).
Singh et al., "Reprogramming CD19-Specific T Cells with IL-21 Signaling Can Improve Adoptive Immunotherapy of B-Lineage Malignancies," Cancer Res., 71(10):3516-3527, (2011).
Ribot et al., "B7-CD28 Costimulatory Signals Control the Survival and Proliferation of Murine and Human γδ T Cells via IL-2 Production," J. Immunol., 189:1202-1208, (2012).
Pistoia et al., "Immunosuppressive microenvironment in neuroblastoma," Front. Oncol., 3(167):1-8, (2013).
Suzuki et al., "Disialoganglioside GD2 as a therapeutic target for human diseases," Expert Opinion on Therapeutic Targets, 19(3):349-362, (2015).
Nedellec et al., "NKG2D Costimulates Human Vγ9Vδ2 T Cell Antitumor Cytotoxicity through Portein Kinase Cθ-Dependent Modulation of Early TCR-Induced Calcium and Transduction Signals," J. Immunol., 185:55-63, (2010).
Wu et al., "An Activating Immunoreceptor Complex Formed by NKG2D and DAP10," Science, 285(5428):730-732, (1999).
U.S. Appl. No. 15/567,165, Non-Final Office Action dated Jan. 3, 2020.
Harly et al., "Molecules and mechanisms implicated in the peculiar antigenic activation process of human Vγ9Vδ2 T cells," Frontiers in Immunology, 5(657):1-13, (2015).
Vanseggelen et al., "On-target off-tumor toxicity; when enhancing an NKG2D-based CAR in vitro led to severe toxicities in vivo," Journal for Immunotherapy, 2(Suppl 3):P15, (2014).
Vantourout and Hayday, "Six-of-the-best: unique contributions of γδ T cells to immunology," Nature, 13:88-100, (2013).
Zhao and Gao, "Research progress of CAR T-cell in tumor therapy," Chin J Clin Oncol, 42(3):190-194, (2015).
Imai et al., "Genetic modification of primary natural killer cells overcomes inhibitory signals and induces specific killing of leukemic cells," Blood, 106(1):376-383 (2005).
Chan et al., "Differential CTLA-4 expression in human CD4+versus CD8+T cells is associated with increased NFAT1 and inhibition of CD4+proliferation," Genes Immun., 15(1):25-32, (2014).
Chang et al., "Targeting the programmed cell death 1: programmed cell death ligand 1 pathway reverses T cell exhaustion in patients with sepsis," Critical Care, 18:R3, 15 pages, (2014).
Farnault et al., "Clinical evidence implicating gamma-delta T cells in EBV control following cord blood transplantation," Bone Marrow Transplant., 48(11):1478-1479, (2013).
Garcia et al., "IL-15 Enhances the Response of Human γδ T Cells to Nonpeptide Microbial Antigens," J. Immunol., 160:4322-4329, (1998).
Haque et al., "Allogeneic cytotoxic T-cell therapy for EBV-positive posttransplantation lymphoproliferative disease: results of a phase 2 multicenter clinical trial," Blood, 110(4):1123-1131, (2007).
Iwasaki et al., "Expression and function of PD-1 in human γδ T cells that recognize phosphoantigens," Eur. J. Immunol., 41:345-355, (2011).
Meraviglia et al., "In vivo manipulation of Vγ9Vδ2 T cells with zoledronate and low-dose interleukin-2 for immunotherapy of advanced breast cancer patients," Clin Exp Immunol., 161(2):290-297, (2010).
Nicol et al., "Clinical evaluation of autologous gamma delta T cell-based immunotherapy for metastatic solid tumours," Br J Cancer, 105(6):778-786, (2011).
Nussbaumer et al., "Essential requirements of zoledronate-induced cytokine and γδ T cell proliferative responses," J. Immunol., 191(3):1345-1355, (2013).
Tanaka et al., "Natural and synthetic non-peptide antigens recognized by human γδ T cells," Nature, 375(6527):155-158, (1995).
Thompson et al., "Activation of γδ T Cells by Bisphosphonates," Osteoimmunoligy, Advances in Experimental Medicine and Biology, Ed. Y. Choi, 658:11-20, (2010).
Tu et al., "The aminobisphosphonate pamidronate controls influenza pathogenesis by expanding a γδ T cell population in humanized mice," J Exp Med., 208(7):1511-1522, (2011).
Wallace et al., "γδ T lymphocyte responses to HIV," Clin Exp Immunol., 103(2):177-184, (1996).
Wang et al., "Indirect Stimulation of Human Vγ2Vδ2 T Cells through Alterations in Isoprenoid Metabolism," J. Immunol., 187:5099-5113, (2011).
Xiang et al., "Targeted activation of human Vγ9Vδ2-T cells controls epstein-barr virus-induced B cell lymphoproliferative disease," Cancer Cell, 26(4):565-576, (2014).
PCT/GB2016/051050 International Search Report and Written Opinion dated Jun. 22, 2016.
Deniger, et al., "Bispecific T-cells Expressing Polyclonal Repertoire of Endogenous γδ T-cell Receptors and Introduced CD19-specific Chimeric Antigen Receptor," *The American Society of Gene & Cell Therapy*, vol. 21, No. 3, 638-647, (Mar. 2013).
Chmielewski, et al., "T cells redirected by a CD3ζ chimeric antigen receptor can establish self-antigen-specific tumour protection in the long term," *Gene therapy*, 20:177-186, (2013).
Long, et al., "4-1BB costimulation ameliorates T cell exhaustion induced by tonic signaling of chimeric antigen receptors," *Nature Medicine*, vol. 21, No. 6, (Jun. 2015).
Fournie, et al., "What lessons can be learned from γδ T cell-based cancer immunotherapy trials?," *Cellular & Molecular Immunology*, 10, 35-41, 2013.
Kunzmann, et al., "Simulation of γδ T cells by aminobisphosphonates and induction of antiplasma cell activity in multiple myeloma," *Blood*, vol. 96, No. 2, (Jul. 15, 2000).
Vanderstegen, et al., "The pharmacology of second-generation chimeric antigen receptors," *Nature Reviews, Drug Discovery*, vol. 14, pp. 499-509, (Jul. 2015).
PCT/GB/2015/051985 International Search Report and Written Opinion dated Oct. 12, 2015.
Kalwak, et al., "CIK cell and γδ T cell expansion in cultures of patients with neuroblastoma and of healthy potential haploidentical haematopoietic cell donors," *Onkol. Pol*, 8, 2: 49-55,(2005). English abstract.
Noguchi, et al., "Zoledronate-activated Vγ9γδ T cell-based immunotherapy is feasible and restores the impairment of gamma-delta T cells in patients with solid tumors," *Cytotherapy*, 13:92-97, (2011).
Nakazawa, et al., "Cytotoxic human peripheral blood-derived γδ T cells kill glioblastoma cell lines: implications for cell-based immunotherapy for patients with glioblastoma," *J Neurooncol*, 116:31-39, (2014).
Wilhelm, et al., "Successful adoptive transfer and in vivo expansion of haploidentical γδ T cells," *Journal of Translational Medicine*, 12:45, (2014).
Yan-Ling, et al., "γδ T Cells and Their Potential for Immunotherapy," *Int. J. Biol. Sci.*, vol. 10, pp. 119-135, (2014).
Database WPI Thomson, "Pharmaceutical, contains (gamma) delta T cell and monoclonal antibody therapeutic agent," Thomson Scientific, London, GB XP002745229, (2009).
Sakamoto et al., "Adoptive Immunotherapy for Advanced Non-small Cell Lung Cancer Using Zoledronate-expanded γδ T Cells: A Phase I Clinical Study," J. Immunother., 34(2):202-211, (2011).
U.S. Appl. No. 15/576,165, Final Office Action dated Oct. 21, 2020.

Figure 1A. Cytotoxic mechanism of classical CAR-expressing γδ T cells

Figure 1B. Cytotoxic mechanism of co-stimulatory CAR-expressing γδ T cells

Figure 3A. Nucleic acid sequence of 'non-tuneable'/'classical' CAR

ATGCTTCTCCTGGTGACAAGCCTTCTGCTCTGTGAGTTACCACACCAGCATTCCTCCTGATCCCAGACATCCAGATG
ACACAGACTACATCCCTCCCTGTCTGCCTCTCTGGGAGACAGAGTCACCATCAGTTGCAGGGCAAGTCAGGACATTAGT
AAATATTTAAATTGGTATCAGCAGAAACCAGATGGAACTGTTAAACTCCTGATCTACAGATTACACTCA
GGAGTCCCATCAAGGTTCAGTGGCAGTGGGTCTGGAACAGATTATTCTCTCACCATTAGCAACCTGGAGCAAGAGAT
ATTGCCACTTACTTTTGCCAACAGGGTAATACGCTTCCGTACACGTTCGGAGGGGACTAAGTTGGAAATAACAGGC
TCCACCTCTGGATCCGGCAAGCCCGGATCTGGCGAGGGATCCACATGCACTGTCTCAGGGTCTCATTACCGACTCAGGACCT
GGCCTGGTGGGCGCCCTCACAGAGCCTGTCCGTCACATGGCTGGGAGTAATATGGGTAGTGAAACCACATACTATAATTCA
TGGATTCGCCAGCCTCCACGAAAGGGTCTGGAGTGGCTGGGAGTAGTGAAACCACATACTATAATTCA
GCTCTCAAATCCAGACTGACCATCATCAAGGACAACTCCAAGAGCCAAGTTTCTTAAAAATGAACAGTCTGCAAACT
GATGACACAGCCATTTACTACTGTGCCAGCGGCGACTTGTATCCTCCTCTATTCCCGGACCTTCTAAGCCCTTTGGGTG
ACCTCAGTCACCGTCTCCTCAGCGGGGAAACACCTTTGTCCAAGTCCCCTATTTCCCGGACCTTCTAAGCCCTTTGGGTG
GAACCATTATCCATGTGAAAGGAGATACGGTGCCTTGCTATAGCTTGCTAGTAACAGTGCCTTTATTTTCTGGGTGAGAGT
CTGGTGGTGGTGGGGGAGTCCTGCACAGTGGCTTGCTATAGCTTGCTAGTAACAGTGCCTTTATTTTCTGGGTGAGAGT
AAGAGGAGCAGGCTCCTGCACAGTGACTACAGTGAACATGACTCCCCGCCCAAGCATTACCAG
CCCTATGCCCACCACGGCGACTTCGCAGCTACTCGCCAGCTAGCTACGGCCAAGAATGGCTGCCGATTTCCAGAGGGCCAGCAA
CCATTTATGAACTGAGAGTGAAGTTCAGCAGGAGAGGAGTACGATGTTTTGGACAAGACGTGGCCGGACCCTGAGATGGGGAAGCCG
TGTGAACTGAGAGTGAAGTTCAGCAGGAGAGGAGTACGATGTTTTGGACAAGACGTGGCCGGACCCTGAGATGGGGAAGCCG
CTCAATCTAGGACGAAGAGGAGTACGATGTTTTGGACAAGACGTGGCCGGACCCTGAGATGGGGAAGCCG
AGAAGGAAGAACCCTCAGGAAGGCCTGTACAATGAACTGTCAGAAAGATAAGATGGCGGAGGCCTACAGTGAGATTGGG
ATGAAAGGCGAGCGCCGGAGGGCAAGGGCACGATGGCCTTTACCAGGGTCTCAGTACAGCCACCAAGGACACCTAC
GACGCCCTTCACATGCAGGCCCTGCCCCCTCGCTAATGA (SEQ ID NO:1)

Figure 3B. Translated protein sequence of 'non-tuneable'/'classical' CAR

<Secretion signal> (SEQ ID NO: 2)
MLLLVTSLLLCELPHPAFLLIP

<Anti-CD19 scFv> (SEQ ID NO: 3)
DIQMTQTTSSLSASLGDRVTISCRASQDISKYLNWYQQKPDGTVKLLIYHTSRLHSGVPSRFSGSGSGTDYSLTISNL
EQEDIATYFCQQGNTLPYTFGGGTKLEITGSTSGSGKPGSGEGSTKGEVKLQESGPGLVAPSQSLSVTCTVSGVSLPD
YGVSWIRQPPRKGLEWLGVIWGSETTYYNSALKSRLTIIKDNSKSQVFLKMNSLQTDDTAIYYCAKHYYYGGSYAMDY
WGQGTSVTVSSAAA <CD28 hinge, transmembrane domain, co-stimulatory domain> (SEQ ID NO: 4)
IEVMYPPPYLDNEKSNGTIIHVKGKHLCPSPLFPGPSKPFWVLVVVGGVLACYSLLVTVAFIIFWVRSKRSRLLHSDY
MNMTPRRPGPTRKHYQPYAPPRDFAAYRS <CD137 (4-1BB) co-stimulatory domain> (SEQ ID NO: 5)
KRGRKKLLYIFKQPFMRPVQTTQEEDGCSCRFPEEEEGGCEL <CD3 zeta activation domain> (SEQ ID NO: 6)
RVKFSRSADAPAYQQGGNQLYNELNLGREEYDVLDKRRGRDPEMGGKPRRKNPQEGLYNELQKDKMAEAYSEIGMKG
ERRRGKGHDGLYQGLSTATKDTYDALHMQALPPR Figure 4A.    Nucleic acid sequence of 'TCR-tuneable'/'co-stimulatory' CAR ATGCTTCTCCTGGTGACAAGCCTTCTGTCTCTGTGAGTTACCACACCAGCATTCCTCTGATCCCAGACATCCAGATG
ACACAGACTACATCCTCCCTGTCTGCCTCTCTGGGAGACAGAGTCACCATCAGTTGCAGGGCAAGTCAGGACATTAGT
AAATATTTAAATTGGTATCAGCAGAAACCAGATGGAACTGTTAAACTCCTGATCTACATCAAGATTACACTCA
GGAGTCCCATCAAGGTTCAGTGGCAGTGGGTCTGGAACAGATTATTCTCACCATTAGCAACCTGGAGCAAGAAGAT
ATTGCCACTTACTTTTGCCAACAGGGTAATACGCTTCCGTACACGTTCGGAGGGGGACTAAGTTGGAAATAACAGGC
TCCACCTCTGGATCCGGCAAGCCCGGATCTGGCGAGGGCGAGGTGAAACTGCAGGAGTCAGGACCT
GGCCTGGTGGCGCCCTCACAGAGCCTGTCCGTCACATGACGTCTCAGGGTCTCATTACCGACTATGGTGTAAGC
TGGATTCGCCAGCCTCCACGAAAGGGTCTGGAGTGGCTGGGAGTAATATGGGGTGAAACCACATACTATAATTCA
GCTCTCAAATCCAGACTGACCATCATCAAGGACAACTCCAAGAGCCAAGTTTTCTTAAAAATGAACAGTCTGCAAACT
GATGACACAGCCATTTACTACTGTGCCAAACATTATTACTACGGTGGTAGCTATGGGACTACTGGGGTCAAGGA
ACCTCACCGTCTCCTCAGCGCGTCTCCTCAGCCGCCAATTGAAGTTATGTATCCTCCTTACCTAGACAATGAGACCCTTTGGGTG
GGAACCATTATCCATGTGAAGGGAAACACCTTTGTCCAAGTCAATTGTGCTAGCTTGCTAGTAACAGTGGCCTTTATTATTTTCTGGGTGAGGAGT
CTGGTGGTTGGGGAGCAGGCCTCGTCCGCACAGTTGAACATGAACTGACTCCCGCCCCCGGCCCCGGCCATTACCAG
AAGAGGAGCAGGCCTCGCACAGTTGAACATGAACTGACTCCCGCCCCCGGCCCCGGCAGAAGAAACTCCTGTATATATTCAAACAA
CCCTATGCCACCACGGACTTCGCAGCTATCGCTCCAAACGGGGCAGAAGAAACTCCTGTATATATTCAAACAA
CCATTTATGAGACCAGTACAACAACTACTCAAGAGGAAGATGGCTGTAGCTGCCGATTTCCAGAAGAAGAAGGAGGA
TGTGAACTGTAATGA    (SEQ ID NO: 7)

Figure 4B. Translated protein sequence of 'TCR-tuneable'/'co-stimulatory' CAR

<Secretion signal> (SEQ ID NO: 8)
MLLLVTSLLLCELPHPAFLLIP

Figure 6:
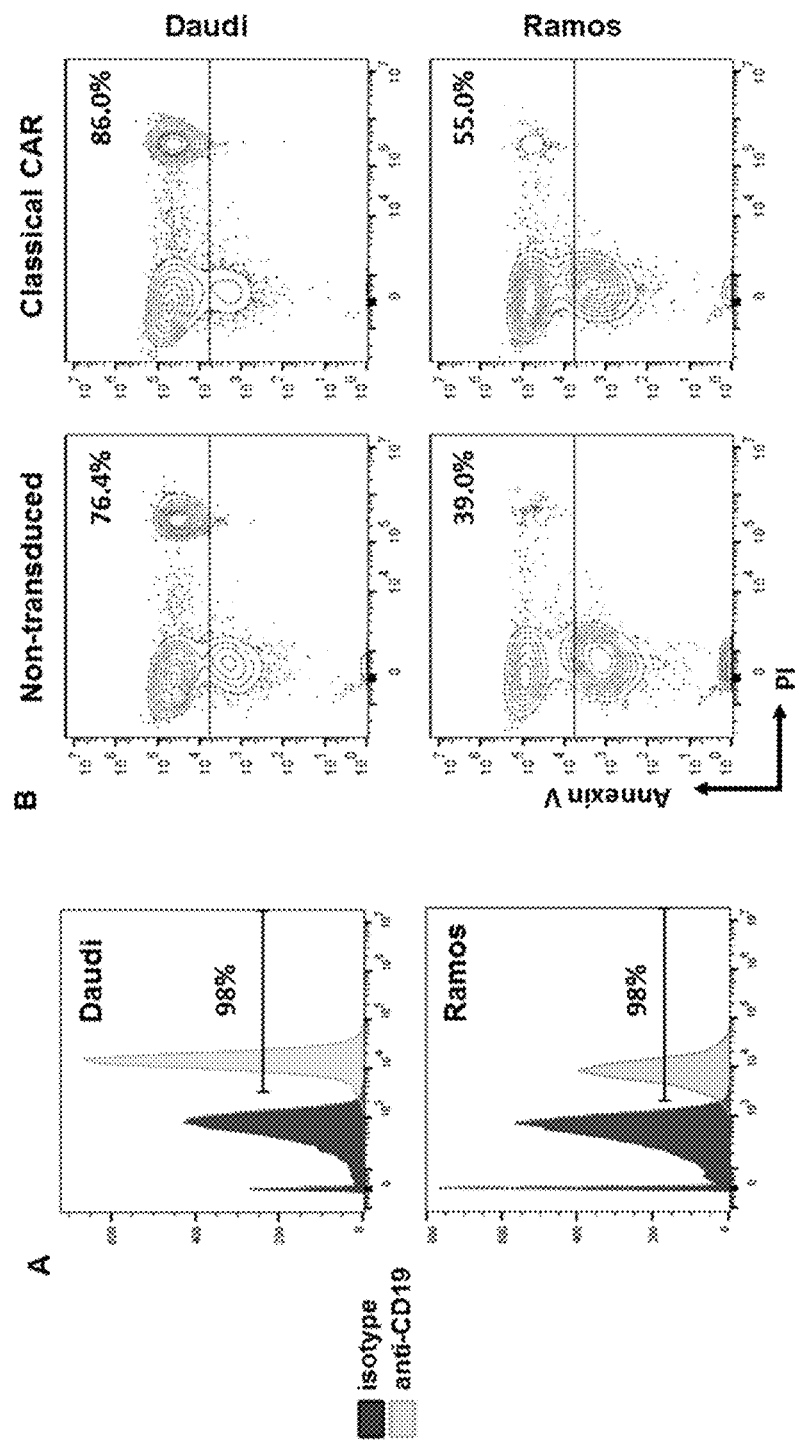

<Anti-CD19 scFv> (SEQ ID NO: 9)
DIQMTQTTSSLSASLGDRVTISCRASQDISKYLNWYQQKPDGTVKLLIYHTSRLHSGVPSRFSGSGSGTDYSLTISNL
EQEDIATYFCQQGNTLPYTFGGGTKLEITGSTSGSGKPGSGEGSTKGEVKLQESGPGLVAPSQSLSVTCTVSGVSLPD
YGVSWIRQPPRKGLEWLGVIWGSETTYYNSALKSRLTIIKDNSKSQVFLKMNSLQTDDTAIYYCAKHYYYGGSYAMDY
WGQGTSVTVSSAAA <CD28 hinge, transmembrane domain, co-stimulatory domain> (SEQ ID NO: 10)
IEVMYPPPYLDNEKSNGTIIHVKGKHLCPSPLFPGPSKPFWVLVVVGGVLACYSLLVTVAFIIFWVRSKRSRLLHSDY
MNMTPRRPGPTRKHYQPYAPPRDFAAYRS <CD137 (4-1BB) activation / co-stimulatory domain> (SEQ ID NO: 11)
KRGRKKLLYIFKQPFMRPVQTTQEEDGCSCRFPEEEEGGCEL Figure 6. Quantitative detection of classical CAR and co-stimulatory CAR expression Figure 7. Potency of classical CAR γδ T cells towards CD19 positive lymphoma cell lines

Figure 8:
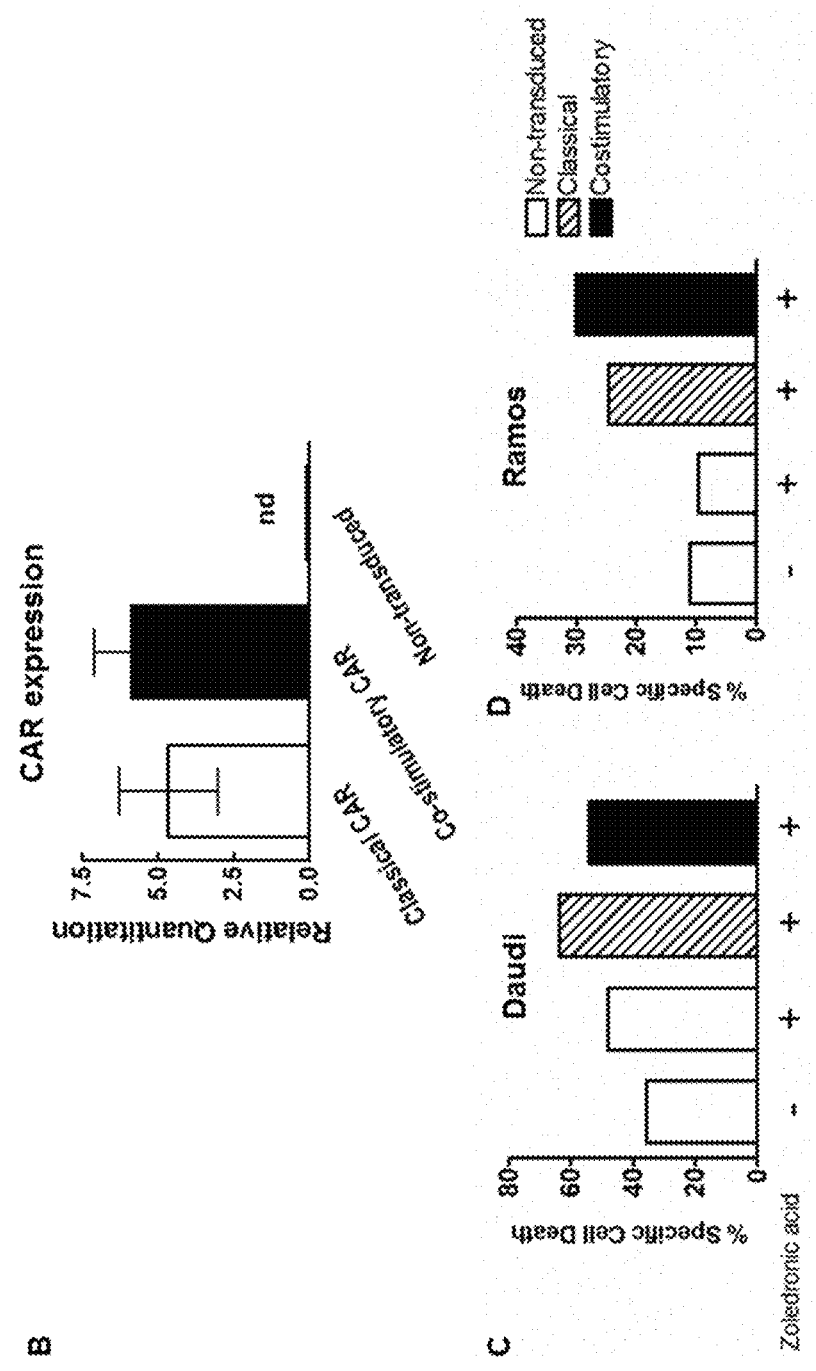

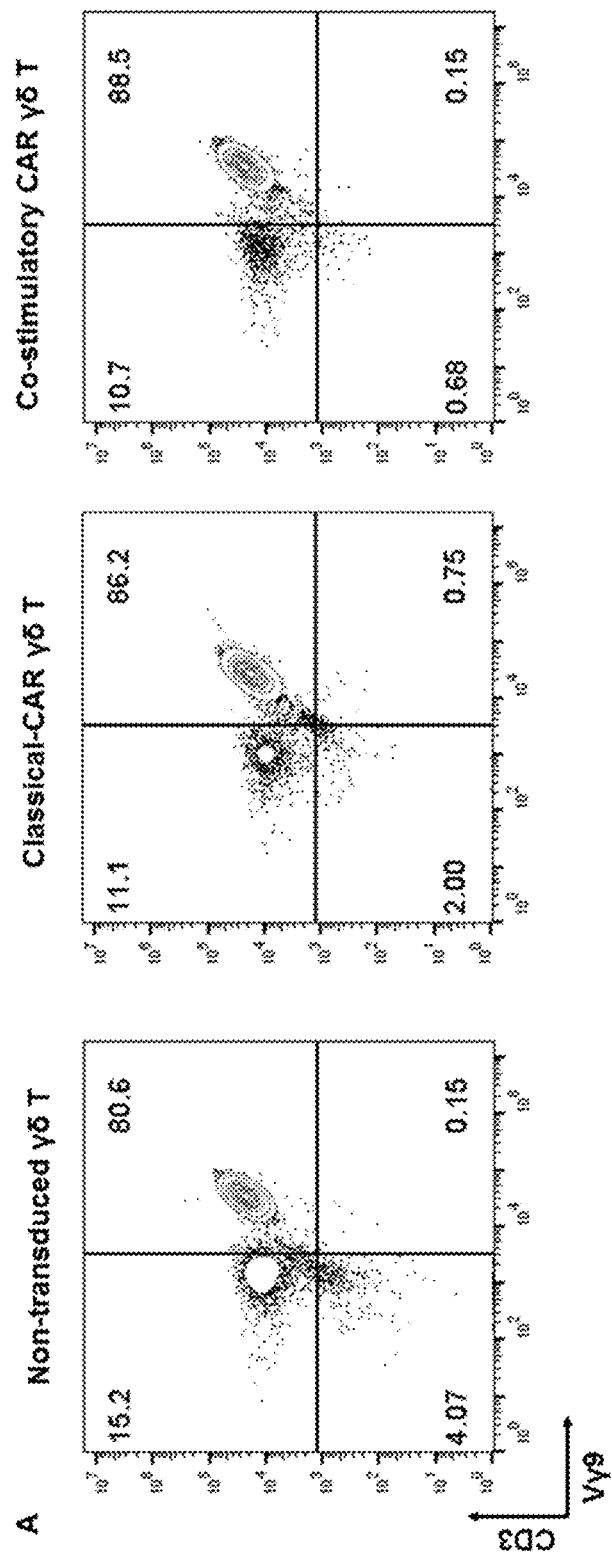
Figure 8. Potency of classical and costimulatory CAR γδ T cells towards CD19 positive lymphoma cell lines

MODIFIED GAMMA DELTA T CELLS AND USES THEREOF

CROSS-REFERENCE TO RELATED APPLICATIONS

This application is a US National Stage entry of International Application No. PCT/GB2016/051050 filed Apr. 14, 2016, which claims the benefit of GB Application No. 1506423.1, filed Apr. 15, 2015, and International Application No. PCT/GB2015/051985 filed Jul. 8, 2015, each of which is herein incorporated by reference in its entirety for all purposes.

REFERENCE TO A SEQUENCE LISTING SUBMITTED AS A TEXT FILE VIA EFS WEB

The Sequence Listing written in file 505532SEQLIST.txt is 14.1 kb, was created on Oct. 12, 2017, and is hereby incorporated by reference.

FIELD OF THE INVENTION

This application relates to methods of preparing and using gamma delta T cells (γδ T cells), suitably the use of gamma delta T cells in allogeneic or autologous recipient subjects for the treatment of conditions including virus infection, fungal infection, protozoal infection and cancer, specifically to the use of chimeric antigen receptors (CARs) modified γδ T cells. The invention also relates to processes for the generation of γδ T cells expressing chimeric antigen receptors and for detecting CAR expression. In addition, the present invention relates to the pharmaceutical use of the cells generated with the processes discussed herein in the treatment of diseases such as cancer and infectious disease.

Gamma delta T lymphocytes represent a minor subset of peripheral blood in humans (less than 10%). Gamma delta T cells expressing Vγ9Vδ2 (gamma 9 delta 2) T cell receptor recognise the endogenous isopentenyl pyrophosphate (IPP) that is over produced in cancer cells as a result of dysregulated mevalonate pathway. The ability of gamma delta T lymphocytes to produce abundant pro inflammatory cytokines like IFN-gamma, their potent cytotoxic effective function and MHC-independent recognition of antigens makes them an important layer of cancer immunotherapy. Gamma delta T cells have been indicated to be able to kill many different types of tumour cell lines and tumour in vitro, including leukaemia, neuroblastoma, and various carcinomas. Further, it has been demonstrated that gamma delta T cells can recognise and kill many different differentiated tumour cells either spontaneously or after treatment with different bisphosphonates, including zoledronate. Human tumour cells can efficiently present aminobisphosphonate and pyrophosphomonoester compounds to gamma delta T cells inducing their proliferation and IFN-gamma production.

Autologous transplantation strategies of gamma delta T cells have been utilised to overcome the disadvantages associated with allogeneic stem cell transplantation. As part of such autologous transplantation techniques, methods of inducing and culturing sufficient numbers of gamma delta T cells for exerting therapeutic effect autologously have been previously disclosed, for example US 2002/0107392. However, autologous treatment strategies suffer from a number of disadvantages.

Thus, alternative and/or improved treatment strategies using gamma delta T cells are required.

SUMMARY OF THE INVENTION

The difficulty of identifying and expanding cancer specific T cell clones has led to the development of Chimeric Antigen Receptors (CARs). CARs use monoclonal antibodies to redirect T cell specificity against target antigens independent of TCR-MHC/peptide recognition. Multiple clinical studies to date have employed CAR transduction of alpha beta (αβ) T cells whilst none have done so using gamma delta (γδ) T cells/lymphocytes. The present inventors have determined that CAR transduction of gamma delta T cells/lymphocytes can be advantageous.

As set out above, the majority of γδ T lymphocytes within peripheral blood are of the Vgamma9 Vdelta2 isotype. γδ T cells expressing the Vgamma9 Vdelta2 T cell receptor recognise the endogenous isopentenyl pyrophosphate (IPP) that is over produced in cancer cells as the result of a dysregulated mevalonate pathway. The inventors consider that the ability of gamma delta (γδ) T lymphocytes to produce abundant pro-inflammatory cytokines like IFN-gamma, their potent cytotoxic effector function and their MHC-independent recognition of antigens makes them an important player in cancer immunotherapy.

Limited in vitro studies have been performed to investigate the ability of CARs to increase the potency of gamma delta (γδ) T cells (Rischer et al., 2004, Deniger et al., 2013). However, such studies have not realised the potential to utilise CAR modified γδ T cells from one subject to provide therapy to a second different subject (allogeneic use). Such studies have further not realised the way in which CAR modified γδ T cells can be provided such that a 'tunable' response is provided.

Accordingly, a first aspect of the present invention provides a modified γδ T cell that expresses a chimeric antigen receptor wherein the chimeric antigen receptor has binding specificity to a disease antigen.

Suitably, a modified γδ T cell may comprise a chimeric antigen receptor wherein the chimeric antigen receptor comprises an extracellular antigen binding domain with binding specificity to a disease antigen, a hinge, a transmembrane domain, and
(i) one or more co-stimulatory signalling regions and a non-functional CD3 zeta activation/signalling domain (tuneable CAR), or
(ii) a CD3 zeta activation/signalling domain, or
(iii) one or more co-stimulatory signalling regions and a functional CD3 zeta activation/signalling domain.

In embodiments a modified γδ T cell can comprise a chimeric antigen receptor wherein the chimeric antigen receptor comprises an extracellular antigen binding domain with binding specificity to a disease antigen, a hinge, a transmembrane domain, one or more co-stimulatory signalling regions and a non-functional CD3 zeta activation domain.

In embodiments the modified γδ T cell can comprise a non-functional CD3 zeta activation domain provided by the absence of a CD3 zeta activation domain in the chimeric antigen receptor.

Suitably, in embodiments the γδ T cell expresses a TCR of any gamma delta TCR pairing from Vγ1 to 9 and Vδ1 to 8. In embodiments the γδ T cell is of the Vγ9Vδ2 subtype.

According to a second aspect of the present invention there is a provided a modified γδ T cell of the first aspect of the invention for use in treatment of conditions such as cancer or infections.

According to a third aspect of the present invention, there is provided a nucleic acid sequence encoding a chimeric antigen receptor (CAR), wherein the CAR is comprised of an extracellular antigen recognition domain such as a single chain variable fragment (scFv), a hinge and transmembrane domain, one or more co-stimulatory signalling regions and optionally CD3 zeta activation domain. Suitable he CD3 zeta domain may also be considered as a CD3 zeta activation or signalling domain. By non-functional CD3 zeta domain, it is considered that signalling is not provided or not sufficiently provided to cause activation.

In embodiments, the nucleic acid sequence can encode a chimeric antigen receptor (CAR), wherein the CAR comprises an extracellular antigen recognition domain, a hinge, a transmembrane domain, and
(i) one or more co-stimulatory signalling regions and a non-functional CD3 zeta activation domain, or
(ii) a CD3 zeta activation domain, or
(iii) one or more co-stimulatory signalling regions and a CD3 zeta activation domain.

In embodiments a non-functional CD3 zeta activation domain can be provided by the absence of a CD3 zeta activation domain in the chimeric antigen receptor.

As stated above, chimeric antigen receptor (CAR) T-cell therapy is an immunotherapy technique wherein T cells are genetically engineered with a synthetic receptor to recognise and target a particular antigen or protein (cell surface target), independent of HLA restriction.

Typically a "classical" $2^{nd}$ or $3^{rd}$ generation CAR is designed in a modular fashion, typically comprising an extracellular target binding domain, usually a single chain variable fragment (scFv), a hinge region, a transmembrane domain which anchors the CAR to the cell membrane and one or more intracellular signalling domains. The signalling domain is usually comprised of elements of the CD3 zeta ($CD3_\zeta$) chain activation domain which provides TCR-like stimulation (termed signal 1) and elements of the CD28, CD137 (4-1BB), CD134 (OX40), CD244 or ICOS signalling moieties that provide co-stimulatory signals (termed signal 2). In such typical CAR expressing T cells, both signal 1 and signal 2 are required to release T cells from a quiescent state. In the absence of additional co-stimulatory signals (signal 2), the presence of signal 1 alone is not sufficient to activate T cells and may render them non-responsive/anergic. Thus, the presence of both signals is necessary to induce T cell activation.

Clinical trials employing CAR expressing T cells (CAR-T) have demonstrated the CAR-T approach and in 2014 anti-CD19 CART cell therapy was approved by the United States' FDA. Whilst impressive response rates have been observed in CAR-T trials, currently the technology is somewhat limited by a lack of true disease antigens i.e. antigens expressed only in disease state cells and not in healthy cells. To date, the vast majority of CAR-T therapies have been CD19 targeted. CD19 is expressed in B cell malignancies but it is also expressed on healthy B cells. In this context, CD19-targeted CAR-T treatment can be tolerated, however patients are suffering an increased risk of infections as their immune system is significantly compromised. This is not the case for the majority of other tumour types, specifically solid tumours, where the targeting of healthy tissue would be intolerable.

A further limitation of CAR-T therapies trialled clinically to date, is the occurrence of relapse due to the development of resistance to the CAR-T therapy. This has been observed in clinical trials of CD19-targeting CAR-T therapy and is achieved by the emergence of cancer cells which exhibit alternate splicing and/or deleterious mutations of the target (CD19) gene. These 'escape variants' result in modified target (CD19) protein which is unrecognisable by the scFv portion of the CAR (whilst retaining sufficient of functionality of the gene). This is a limitation of any single targeting approach; in the context of proliferating cells i.e. cancer, this provides a positive selective pressure to abrogate target antigen expression.

The present invention exploits the natural ability of γδ T cells to specifically recognise stressed/diseased cells (i.e. cancer cells or infected cells) in combination with the potent, antigen directed cytotoxic effector function of chimeric antigen receptor technology. A γδ T cell transduced with a classical CAR exhibits enhanced effector functions against target cells expressing the CAR-triggering antigen and increased persistence in vivo. The inventors consider CAR modified gamma delta T cells could render cancerous or infected cells, which may be resistant to normal γδ T cells, susceptible to γδ T cell-mediated killing. Suitably, without wishing to be bound by theory, the inventors consider that a γδ T cell co-expressing a classical CAR will be capable of recognising, and therefore targeting for cytolysis, cells expressing either phosphoantigens or a CAR-directed antigen, thus increasing the range of cells which may be targeted by such modified gamma delta T cells. It is further considered that a limitation of existing CAR-T therapies, the development of resistance due to positive selection of cancer cells that do not express the CAR antigen, will be mitigated by CAR-expressing γδ T cells that will have dual antigen specificity. Suitably such CAR modified gamma delta T cells could be provided to an allogeneic subject, i.e. a different subject to that from which the gamma delta T cells were first obtained.

As will be appreciated by those of skill in the art, the effects obtained by provision of CAR sequence(s) to a γδ T cell and the use thereof as discussed herein, may be suitably obtained by provision of a CAR sequence to a γδ T-like cell. Suitably, a γδ T-like cell may include any cell genetically engineered to express a functional γδ TCR. For example, an αβ T cell or NKT cell genetically engineered to express a functional γδ TCR thus re-directing the specificity of the cell to defined γδ TCR antigens, such as IPPs in the context of a Vgamma9Vdelta2 TCR.

Conventional CAR-T technology is considered to be encumbered by a number of safety issues which hinder the success of the approach when applied in vivo, namely "on-target" but "off-tumour" toxicity, due to expression of the CAR-triggering antigen on healthy tissues. In embodiments, there is provided a CAR modified gamma delta T cell in which the $CD3_\zeta$ domain has been removed o rendered non-functional, whilst retaining the MHC-independent antigen recognition function (e.g. via the scFv) and the co-stimulatory function (via one or more co-stimulatory domains).

In embodiments a non-functional or inactive CD3zeta domain is unable to provide signal 1 as discussed herein. Suitably, there may be provided a modified γδ T cell comprising a chimeric antigen receptor wherein the chimeric antigen receptor comprises an extracellular antigen binding domain with binding specificity to a disease associated antigen, a hinge, a transmembrane domain, one or more co-stimulatory signalling regions and absence of a functional signal 1 providing domain. As would be appreciated by a person of skill in the art, signal 1 may be provided by a CD3 zeta domain or the like.

In such embodiments the CAR is incapable of providing signal 1 whilst retaining signal 2 function from the presence of one or more co-stimulatory domains. Advantageously this leads to inability for the CAR to elicit cytotoxic effector function in the absence of a TCR signal/signal 1. Without wishing to be bound by theory, the inventors consider that whilst this CAR design would be ineffective in a polyclonal αβ T cell population due to lack of signal 1, the expression of such a CAR in an in vitro expanded γδ T cell population provides for an effective CAR when the γδ TCR is activated. In embodiments a CAR-expressing γδ T cell, in which the CAR CD3$_\zeta$ domain has been removed or rendered inactive or non-functional, of the Vγ9Vδ2 isotype can be provided. In such embodiments, signal 1 can be provided by phosphoantigen stimulation of the Vγ9Vδ2 TCR. In such embodiments, suitably only in the presence of phosphoantigens may the CAR elicit cell-mediated cytolysis and cytokine production. Suitably, such a CAR design may exploit the defined specificity of Vγ9Vδ2 T cells towards phosphoantigens (present only on stressed cells) and permit activation which can be tuned by T cell receptor signalling.

In embodiments it is proposed a gamma delta T cell of the present invention, in particular a Vγ9Vδ2 cell or cell populations of gamma delta T cells can be modified to comprise a chimeric antigen receptor to direct the gamma delta T cell against a particular antigen or protein (cell surface target(s) (wherein cell surface target(s) can include a ligand(s) found in a particular cell environment (i.e. tumour environment), but not linked to a target cell)). In embodiments the cell surface target can be joined to the target cell. This allows the chimeric antigen receptor (CAR) gamma T cell to be brought into proximity with the target cell, in particular a target cell including the cell surface target and to trigger the activation of the gamma delta T cell. Such chimeric antigen receptor (CAR) gamma T cells form an aspect of the present invention.

In embodiments the antigen recognition domain of the CAR construct can be a single chain variable fragment (ScFv) or fragment-antigen binding (Fab) domain selected from libraries that specifically recognise and are capable of binding to a cell surface target or natural ligand that engages its cognate receptor on the target cell.

In embodiments a disease antigen bound by a chimeric antigen receptor as discussed herein can be a cell surface target, a disease associated antigen, for example an antigen associated with a disease state, for example in cancer or in an infection wherein the disease associated antigen can be on or in the vicinity of a cell to be targeted by the γδ T cell such that the γδ T cell can target said cell to be targeted. In embodiments a cell surface target can be an antigen found in a cell infection, bacterial infection, fungal infection or protozoan infection or can be an active or inactivated viral fragment, a peptide, a protein, an antigenic segment or the like from such a virus. Alternatively the cell surface target may include a tumour-specific antigen and/or tumour associated antigen.

In embodiments the CAR, for example ScFv provided on the extracellular surface of the gamma delta T cell can be connected via a spacer or fused directly to a transmembrane domain which traverses the cell membrane and connects to an intracellular signalling domain.

In embodiments the CAR, for example the ScFv can be fused via a transmembrane domain to a CD3 zeta (providing signal 1) and co-stimulatory immunoreceptor tyrosine-based activation motif (ITAM) (signal 2).

A CAR is generally considered to redirect the T cell specificity to the cell surface target and overcomes issues relating to T cell tolerance. As will be appreciated, the cell surface target typically can be selected to ensure targeting of the gamma delta T cell towards cells of interest, e.g. tumour cells or virally infected cells, in preference to healthy cells.

As will be appreciated, both on, for example a target tumour cell and normal tissue, where a cell surface target is expressed, chimeric antigen receptor technology, whilst highly potent, can be susceptible to "on target, off-tumour toxicity".

As discussed above, in CAR targeting systems where the chimeric antigen receptor fuse signal 1 and signal 2 components into a single construct, they can provide highly potent and sensitive target-dependent effector responses. However, such CAR targeting systems are not tuneable to the level of cell surface target expressed on a target cell.

It is considered that Vγ9Vδ2 TCR-mediated recognition provides a further CAR independent targeting strategy that allows the CAR response to be "tuned" such that a stimulating signal from the CAR will translate to a functional response only in the context of Vγ9Vδ2 TCR stimulation. This allows, for example a broad range of tumour targets (HMBPP/IPP stress related pathway targets) to be targeted with an additional cell surface target by a CAR-modified gamma delta T cell. These CAR modified gamma delta T cells of the invention provide a tunable response, wherein for a given tumour-associated antigen, pyrophosphate/phosphonate (drug) dose there is generated a suboptimal signal 1 strength response, with an ability to synergise with signal 2 from a specific "co-stimulatory CAR".

In embodiments in vitro activation assays may be used to determine relevant drug doses for optimal "tuning response", to allow maximum discrimination between target tumour lines expressing high levels of the tumour associated antigen (higher signal 2 strength) and relevant non-transformed cells expressing lower levels (generating lower signal strength). In embodiments, multiple CARs could be utilised to target different tumour/cell types. Such multiple CARs could be provided on one gamma delta T cell, in particular Vγ9Vδ2 cell, or multiple gamma delta T cells, in particular Vγ9Vδ2 cells, with different CARs on each cell (a treatment bank) could be generated and the respective CAR gamma delta cell used for a particular tumour and/or cell type.

It is considered that expression of a heterodimeric γδ TCR on a gamma delta T cell that does not recognise MHC molecules means such gamma delta cells are capable of mounting a potent effector response. In particular such cells (e.g. Vγ9Vδ2) can be highly cytotoxic, producing high levels of Th1 cytokines including 1FNγ and TNFα.

In embodiments a gamma delta T cell can further comprise an inhibitory chimeric antigen receptor (ICAR), wherein the ICAR minimises activation in off-target cells e.g. non tumour cells wherein the cell surface target is a tumour-associated, but not tumour-specific antigen. To minimise for example, such "on target, off tumour toxicity" the presence of a second antigen on an off target cell which can be bound by the inhibitory CAR will cause the signal provided by any binding of the CAR to the cell surface target to be inhibited.

In embodiments, the gamma delta cell can comprise a further CAR capable of binding to a different antigen present on a target cell or to soluble signalling proteins present in, for example, a tumour or virally infected cell environment, e.g. IL-12 that can stimulate gamma delta T cell activation and recruitment.

In embodiments the gamma delta T cell with at least a first chimeric antigen receptor and optionally at least a first inhibitory chimeric antigen receptor, is a Vγ9Vδ2 T cell.

Provision of chimeric antigen receptor to a gamma delta T cell can be by means known in the art to provide chimeric antigen receptors to T cells.

Accordingly to a fourth aspect of the invention, there is provided a process to provide a CAR modified γδ T cell wherein the nucleic acid of the third aspect is incorporated/transduced into a γδ T cell to genetically modify the γδ T cell. Suitably, the process can utilise a lentiviral CAR construct. Suitably, the process simultaneously transduces a CAR construct into a cell, and selectively expands CAR-transduced γδ T cells.

It is considered embodiments of the process will enable a 'TCR-tuneable' or 'co-stimulatory' CAR to be provided.

As discussed above, in such embodiments, γδ T cells expressing a co-stimulatory CAR will be activated only in the presence of phosphoantigens (present on the cell surface during infection or cancer) but not by healthy cells. It is considered this will circumvent the "on-target" but "off-tumour" toxicity observed in conventional CAR-T therapies. In such embodiments, it is considered the activity of the co-stimulatory CAR can be tuned by concomitant TCR signalling through the γδ T cell receptor.

In embodiments of the third aspect of the invention, the nucleic acid sequence encoding a CAR may include a leader sequence which will direct the protein to the cell membrane (such as the GMCSF-R secretory signal or CD8), an antigen binding domain, a hinge and transmembrane domain, one or more co-stimulatory signalling regions and the presence or absence of a CD3 zeta signalling domain. As discussed herein, the absence of a CD3 zeta signalling domain may be provided by an inactive or non-functional CD3 zeta domain.

In embodiments of the nucleic acid including the CD3 zeta domain, the CAR is considered 'classical' or 'non-tuneable'. In embodiments in which the CD3 zeta domain has been omitted, the CAR is a 'co-stimulatory' or 'TCR-tuneable' CAR.

In embodiments, a nucleic acid sequence encoding the 'classical' or 'non-tuneable' CAR can comprise a scFv recognising the B cell protein CD19. In specific embodiments a "classical" CAR can comprise the nucleotide sequence SEQ ID NO: 1, which can suitably encode the amino acid sequences SEQ ID NOS: 2 to 6.

In embodiments wherein the nucleic acid sequence encodes the 'co-stimulatory' or 'TCR-tuneable' CAR, the nucleic acid can comprise a scFv recognising the B cell protein CD19. In specific embodiments the nucleic acid sequence can comprise the nucleotide sequence SEQ ID NO: 7, which can encode the amino acid sequences SEQ ID NOS: 8 to 11.

In embodiments, the nucleic acid can encode an extracellular antigen binding domain that is a single scFv that specifically recognises and is capable of binding to a cell surface target. Suitably in embodiments, the extracellular antigen binding domain, preferably a scFv, recognises and binds to the B cell antigen CD19 previously described clone known as FMC63 (Nicholson I C et al., 1997).

In embodiments, the antigen binding domain of the CAR binds to a cell surface target, tumour antigen and/or tumour associated antigen. In embodiments a cell surface target can be an antigen found in a cell infection, bacterial infection, fungal infection, protozoan infection or virus infection or can be an active or inactivated viral fragment, a peptide, a protein, an antigenic segment or the like from such a virus.

Suitably, in embodiments of the present invention the extracellular antigen binding domain can recognise and bind to a tumour-specific antigen which is present only on tumour cells and not on any other cells and/or a tumour-associated antigen which is present on some tumour cells and also some normal cells. Such tumour specific antigens may include, but are not limited to, CD19, EGFRvRIII, ErbB2, GM3, GD2, GD3, CD20, CD22, gp100, NY-ESO-1, carbonic anhydrase IX, WT1, carcinoembryonic antigen, CA-125, MUC-1, MUC-3, epithelial tumour antigen and a MAGE-type antigen including MAGEA1, MAGEA3, MAGEA4, MAGEA12, MAGEC2, BAGE, GAGE, XAGE1B, CTAG2, CTAG1, SSX2, or LAGE1 or viral antigens or combinations thereof or post-translationally modified proteins that may include, but are not limited to, carbamylated and citrunillated proteins.

In embodiments, the cell surface antigen can be an immune checkpoint ligand, for example PD-L1.

In embodiments, the antigen binding domain may be the extracellular portion of a cell surface receptor which is then fused to the transmembrane and co-stimulatory domains as described above.

In embodiments the transmembrane domain of the CAR can comprise one or more of the transmembrane domains of CD3 or CD4 or CD8 or CD28.

In embodiments the costimulatory signalling region of the CAR can comprise one or more of the intracellular domains of CD28, CD137 (4-1BB), ICOS, CD27, OX40, LFA1, PD-1, CD150, CD244, NKG2D.

Suitably, γδ T cells for use in the invention may be generated from blood mononuclear cells (BMCs) or biopsies from cancer or infected tissues. Suitably, BMCs may be obtained via any density centrifugation method known to those skilled in the art from either whole blood, leukapheresis material or umbilical cord blood (UCB). Density centrifugation methods may include, but are not limited to, ficoll gradient or lymphoprep. In addition, cell isolation can be performed by magnetic-activated cell sorting (MACS) or fluorescence-activated cell sorting (FACS).

Suitably, in embodiments γδ T cells may be expanded from peripheral blood mononuclear cells (PBMCs), cord blood mononuclear cells (CBMCs) or tissue derived cells in a chemically defined culture medium which can include, but is not limited to, RPMI, TexMACS, IMDM, CTS OpTmizer or AIM-V media. Cell culture medium can be supplemented with either foetal calf serum (FCS), human AB serum, autologous plasma, human platelet lysate or chemically defined serum replacement substitutes for example. Further, serum/plasma/substitute is added in an amount of 0.1 to 20% (v/v) to the culture solution.

Suitably, in embodiments γδ T cells of the Vgamma9 subtype may be selectively expanded from PBMCs or CBMCs or tissue derived cells in a chemically defined culture medium, including IL-2, serum/plasma and activation by the provision of an aminobisphosphonate such as zoledronic acid. Multiple γδ TCR isotypes may be used from any gamma delta TCR pairing from Vγ1-9 and Vδ1-8. It will be understood by those of skill in the art that culture conditions, specifically the method of TCR activation, will define the isotype to be expanded. By way of example, δ2 T cells are activated and expanded by aminobisphosphonates and the like, whilst δ1 T cells may be preferentially expanded using NKG2D ligands such as MICA or MICB. Isolated PBMCs/CBMCs may be freshly isolated or cryopreserved prior to expansion in culture.

A bisphosphonate is an analogue of pyrophosphoric acid and is a compound in which the O (oxygen atom) of the pyrophosphoric acid skeleton P—O—P is substituted with C (carbon atom) (P—C—P). It is generally used as a therapeutic drug for osteoporosis. The aminobisphosphonate refers to a compound having N (nitrogen atom) among the bisphosphonates. For example, the aminobisphosphonate used in the present invention is not particularly limited; examples thereof include pamidronic acid, its salt and/or their hydrate, alendronic acid, its salt and/or their hydrate, and zoledronic acid, its salt and/or their hydrate. The concentration of the aminobisphosphonates is preferably 1 to 30 µM for pamidronic acid, its salt and/or their hydrate, 1 to 30 µM for alendronic acid, its salt and/or their hydrate, and 0.1 to 10 µM for zoledronic acid, its salt and/or their hydrate. Here, 5 µM zoledronic acid is added as an example.

Suitably, the cytokine IL-2 may also be included at 50 IU/ml to 2000 IU/mL, more preferably 400 IU/mL to 1000 IU/mL. Suitably, the culture may also be supplemented with one or more cytokines such as IL-15, IL-18 or IL-21 at 50 IU/ml to 2000 IU/ml.

Suitably, antigen provision via aminobisphosphonate may be substituted with synthetic antigens such as isopentenyl pyrophosphate (IPP), phosphostim/bromohydrin pyrophosphate (BrHPP), (E)-4-Hydroxy-3-methyl-but-2-enyl pyrophosphate (HMBPP) or DMAPP. Antigenic stimulation may also be provided by co-culturing with irradiated and/or artificial antigen presenting cells (aAPC). The addition of such components provides a culturing environment which allows for positive selection of gamma delta T cells typically at 70%-100% by number of total cells in the culture sample.

The expansion of γδ T cells may be also stimulated with one or more antibodies against CD3, gamma delta TCR, CD28 and CD137. These can be soluble, plate bound or conjugated to appropriate beads, such as dynabeads or MACSibeads. γδ T cells may be propagated and expanded using any of the methodologies previously disclosed.

Suitably, CAR-expressing cells can be selectively expanded with the use of a recombinant protein recognised by the CAR e.g. recombinant CD19-Fc chimera or recombinant CD19 in the case of a CD19-targeted CAR. This can be plate bound, soluble or on appropriate beads, such as dynabeads or MACSibeads. γδ T cells of any isotype may be selectively expanded for a time-frame of at least 7 days, more preferably 14 days. Suitably, the period of culturing may be performed for about 9 days or greater to achieve high numbers of substantially purified CAR-expressing gamma delta T cell populations. γδ T cells may be expanded using TCR antigens or NKG2D ligands such as MICA or MICB. Isolated PBMCs may be freshly isolated or cryopreserved prior to expansion in culture. Expanded γδ T cells may be cryopreserved and resuscitated at a later time point for further expansion in culture.

The method of genetically modifying a γδ T cell to incorporate the nucleic acid encoding a CAR design may include any technique known to those skilled in the art. Suitable methodologies include, but are not restricted to, viral transduction with lentiviruses/retroviruses/adenoviruses, cellular transfection by electroporation, lipid-based transfection reagents, nanoparticles, calcium chloride based transfection methods or bacterially-derived transposons.

In embodiments when lentiviruses/retrovirus/adenovirus can be employed for transduction, inclusion of chemical reagents as would be understood by those in the art to enhance this process can be used. These include for example, but are not limited to, hexadimethrine bromide (Polybrene), recombinant human fibronectin (such as RetroNectin-Takara Clontech) and TransPlus Virus Transduction Enhancer (ALSTEM Cell Advancements).

Suitably, incorporation of nucleic acid encoding a CAR may be introduced to PBMCs, CBMCs or tissue derived expanded γδ T cells at any time-point over the culturing period.

Detecting the efficiency of the transduction and expression of the CAR constructs by the γδ T cells may include any technique known to those skilled in the art and can include, but is not restricted to, quantitative PCR and antibody based detection methods such as flow cytometry or western blotting.

According to an aspect of the invention there is provided a method to detect between classical CAR and co-stimulatory CAR using at least one primer pair selected from the group SEQ ID NO: 12 and SEQ ID NO: 13, and SEQ ID NO:14 and SEQ ID NO: 15.

```
Forward
                                         (SEQ ID NO: 12)
   5'-GCTCCTGCACAGTGACTACAT-3'

Reverse
                                         (SEQ ID NO: 13)
   5'-GGAGTTTCTTTCTGCCCCGT-3'

Forward
                                         (SEQ ID NO: 14)
   5'-CTGTAGCTGCCGATTTCCAGA-3'

Reverse
                                         (SEQ ID NO: 15)
   5'-CATCGTACTCCTCTCTTCGTCC-3'
```

Suitably, said method may allow the quantitative detection of classical CAR and co-stimulatory CAR. Suitably said method allows the discrimination between classical CAR and co-stimulatory CAR.

In one embodiment flow cytometry can be employed, for example an antibody against the idiotype of the scFv can be used, which is conjugated to a fluorochrome or antigen that can be detected with a secondary reagent, such as fluorescently labelled-streptavidin. In embodiments the reagent used to detect the CAR can be a chimeric protein comprising of the recombinant protein recognised by the CAR, fused with a mammalian antibody Fc fraction, e.g. CD19-Fc chimera. This can be detected with an antibody against the Fc-portion of the protein. These reagents can be combined with fluorochrome conjugated antibodies against immunophenotyping markers that can include but are not limited to Vgamma9, CD3, gamma delta TCR, alpha beta TCR, CD4, CD8 and CD56.

Methods of Treatment Using CAR Modified Gamma Delta Cells

In embodiments, of the second aspect of the invention, a tuneable/co-stimulatory CAR or classical CAR expressing γδ T cells can be administered to a patient in order to treat a disease such as a viral, bacterial, fungal or protozoan infection or cancer.

In embodiments, a tuneable/co-stimulatory CAR expressing γδ T cell(s) can be co-administered to a subject with an aminobisphosphonate, or substitute thereof, wherein the substitute is capable of enhancing the levels of phosphoantigens present on the target cells via dysregulation of the physiological mevalonate pathway. It is considered such co-administration may be advantageous to leverage Vγ9Vδ2 TCR recognition to enable 'drug-tuneable' titration of signal 1 strength from the phosphoantigen engaged γδ TCR. The tuneable/co-stimulatory CAR can provide a novel signal 2-restricted to cells based on the CAR-targeted disease-associated antigen.

In specific embodiments, for a given disease-associated antigen, an aminobisphosphonate dose or a substitute thereof can be tailored to generate suboptimal signal 1 strength, to synergise with signal 2 from a specific tuneable/co-stimulatory CAR. In vitro activation could be used to estimate relevant drug doses for optimal 'tuning', to allow maximum discrimination between disease-associated antigen expressing cell lines expressing high levels of the antigen (higher signal 2 strength) and non-transformed cells expressing lower levels (generating lower signal 2 strength). For example, the co-administered aminobisphosphonate used in the present invention may include zoledronic acid, its salt and/or their hydrate, alendronic acid, its salt and/or their hydrate, and pamidronic acid, its salt and/or their hydrate.

It is considered that allogeneic use of gamma delta T cells of the present invention in therapy, wherein said gamma delta cells use CAR modified gamma delta T cells of the present invention has not been considered typically due to potential problems linked to immune-system mediated rejection. The inventors consider that gamma delta T cells do not typically cause graft versus host disease, and that the selection of gamma delta T cells for allogeneic transplantation would allow T cells to be provided to a recipient with a minimal risk of graft versus host disease. It is considered that as the gamma delta T cells are not MHC restricted, allogeneic transplantation will be a viable therapy wherein gamma delta T cells are capable of targeting cells for cytolysis independently of MHC-haplotype. In view of the lack of recognition of MHC-presented antigens by gamma delta T cells, the present inventors consider that the risk of GVHD would be minimised in a high purity allogeneic transfer of gamma delta T cells sufficiently purified from other leukocytes including B cells and alpha beta T cell receptor (TCR) T cells. Additionally, it is considered there will be a low chance of graft rejection due to the immune-compromised state of the recipient in certain disease states, including but not limited to patients with severe viral infections, for example Ebola, HIV and influenza as well as PTLD-EBV patients and those with other cancer types.

As noted, previous treatment strategies have included T cell removal from donor blood, in particular peripheral blood, using a negative selection or positive selection methodology, prior to allogeneic stem cell transplantation.

There is provided a method of treatment comprising; collection of cells from a donor subject, processing of such donor cells to allow the provision of sufficient numbers of gamma delta T cells allogeneically to a recipient subject, wherein said processing includes the step of modifying the gamma delta T cells to incorporate a Chimeric Antigen Receptor such that the modified gamma delta T cells can be provided to the allogeneic subjects to exert a therapeutic effect to the recipient subject.

By way of example, the gamma delta T cell expansion method may comprise the isolation of peripheral blood mononuclear cells (PBMCs) from blood or leukapheresis material using density gradient centrifugation. Isolated PBMCs may be cryopreserved prior to expansion in culture, whilst plasma is co-extracted and retained as an autologous excipient for use in subsequent gamma delta T cell culturing steps. In embodiments freshly isolated PBMCs (or those resuscitated from cryopreservation) can be inoculated into growth media containing human recombinant IL-2 (e.g. at a concentration of up to 1000 U/ml) and zoledronic acid (e.g. 5 µM). The γδ T lymphocyte population may be activated and selectively proliferated from the PBMCs via the addition of zoledronic acid (day 0) and the continuous inclusion of IL-2 over a 14 day culture period. The cell suspension may be serially expanded (typically at a 1:2 split ratio) over this time period. 14 days after culture initiation the cells can be harvested and resuspended in lactated ringers solution and HSA prior to transfer to an infusion bottle containing 100 ml saline solution. Alternatively, cells may be cryopreserved for resuscitation at a later time.

Following expansion, in embodiments, the gamma delta T cell product meets the following minimum specifications; greater than 80% of total cells are T lymphocytes (CD3 positive), gamma delta T lymphocytes comprise 60% or greater of the total T lymphocyte population (Vgamma9 positive), NK cells are less than 25% of the total T lymphocyte population (CD3 negative/CD56 positive), Cytotoxic T cells are below 10% of total T lymphocyte population (CD3/CD8 positive) and T helper cells are below 5% of total T lymphocyte population (CD3/CD4 positive). In embodiments, cell populations meeting these specifications can be used as the starting material for the generation of high purity allogeneic cell banks which will aim to have greater than 99% gamma delta T cells.

Accordingly, there is provided a process for providing gamma delta T cells allogeneically to a second subject comprising the steps
 providing a sample of gamma delta T cells from a first subject;
 culturing the gamma delta T cells to allow them to be administered to a second subject, wherein the gamma delta T cells are modified to provide CAR modified gamma delta T cells.

In embodiments, the step of providing can include a step of collecting gamma delta T cells from a first subject. The collection can be from a donor subject wherein the donor subject has no immediate perceived health conditions. Suitably the recipient subject may be a vertebrate, for example a mammal, for example a human, or commercially valuable livestock, a research animal, a horse, cow, goat, rat, mouse, rabbit, pig, and the like. In embodiments the first and second subjects can be human. As will be understood, in the context of the present invention, the first subject is a donor subject from whom gamma delta T cells are collected, and the cells are used in the allogeneic treatment of a different second (recipient) subject. Suitably, the first subject has a pre-disease state. The term "pre-disease" state as used herein covers the absolute term of "healthy", "no disease", "and the relative term of a graduation in a disease potential progression", "healthier than" or "less diseased than" a post diseased state. Since "pre-disease" can be defined by a time prior to the first subject being diagnosed with a disease, the first subject can be healthy in an absolute term or might already have the disease where the disease is not yet manifested itself or been diagnosed or detected. In embodiments the process can comprise the step of culturing gamma delta T cells obtained from the first subject to allow the gamma delta T cells to be provided to the second subject.

In embodiments the gamma delta T cells can be collected from peripheral blood or peripheral blood mononuclear cells obtained following apheresis or leukapheresis or from umbilical cord blood. Ex vivo expansion of gamma delta T cells from peripheral blood will preferentially give rise to gamma delta T cells of the Vγ9Vδ2 phenotype when activated with phosphoantigens or aminobisphosphonates. The use of umbilical cord blood as starting material for ex vivo expansion permits the selective expansion of several T cell receptor (TCR) subtypes dependent upon the activating antigen. These TCR isotypes may include may include any gamma delta TCR pairing from Vγ1-9 and Vδ1-8, for example, but not limited to Vδ1, Vδ2 and Vδ3 TCR variants. Gamma delta T cells of discrete subtypes recognise distinct antigens and would therefore exhibit differing levels of cytotoxicity dependent upon the antigens presented by the target cells. The relative abundances of each delta TCR subtype is dependent largely upon the culturing conditions and specific antigens presented. Culturing conditions may be tailored to preferentially expand a desired TCR isotype from umbilical cord blood. For example, gamma delta T cells expressing a singular TCR isotype may be more efficacious in the treatment of a particular cancer type or for the treatment of a specific viral infection.

In embodiments the collecting step can comprise the step of administering to the first subject a gamma delta T cell potentiating agent, prior to collecting the gamma delta T cells from the first subject.

In embodiments the method of collecting the gamma delta T cells can comprise the step of administering to the first subject a potentiating agent such as a growth factor which induces white cell mobilization from the bone marrow such as G-CSF, an aminobisphosphonate, in particular pamidronic acid, alendronic acid, zoledronic acid, risedronic acid, ibandronic acid, incadronic acid, a salt therefor and/or a hydrate thereof.

In an embodiment processing or the process can comprise any one or more of the steps of:—
providing blood, for example umbilical cord blood or apheresis/leukophoresis derived cells from a first subject (donor),
separating peripheral blood mononuclear cells from the blood,
adding amino bisphosphonate and a target antigen to the peripheral blood mononuclear cells, and
culturing the peripheral blood mononuclear cells to proliferate/induce target antigen specific cytotoxic T cells (CTLs) and gamma delta T cells,
modifying the gamma delta T cells to provide CAR modified gamma delta T cells as discussed herein, and optionally co-culturing the PBMCs or CBMCs or T cells with artificial antigen presenting cells (aAPC) to proliferate/induce target antigen specific cytotoxic T cells (CTLs) and gamma delta T cells.

The present inventors consider that providing gamma delta T cells that are substantially isolated from other components of whole blood will reduce the graft failure when those substantially isolated gamma delta T cells are allogeneically administered to a second subject. Consequently, the process of the present invention may include a step of purifying gamma delta T cells from whole blood, or components thereof. As less than 10% of peripheral blood by total number of cells is composed of gamma delta T cells, purifying a sample of whole blood, or components thereof, for example using anti-gamma delta T cell antibodies so that more than 10% by mass of the sample consists of gamma delta T cells is considered to enhance the effectiveness of allogeneically treating the recipient subject. Consequently, the process for the present invention may include the step of purifying a sample of whole blood, or components thereof, in order to achieve a greater than 10, 25, 50, 75, 85, 90, 95 or 98% of the total number of cells in the purified sample being gamma delta T cells.

Any method known to the skilled person that is capable of purifying gamma delta T cells from whole blood, umbilical blood or components thereof, can form part of the present invention. Clearly, the purification step should not affect or minimally affect the viability of the gamma delta T cells. For example, the following steps may be used in combination, or alone, to achieve the aforementioned purification of the gamma delta T cells: —a process of dialysis (e.g. apheresis and/or leukapheresis); differential centrifugation; growth of gamma delta T cells in culture (eg preferential growth in culture).

The step of purification can, at least in part, be carried out during the culturing step. For example, during the culturing step, addition of at least one or a combination of specific components such as aminobisphosphonate in particular pamidronic acid, alendronic acid, zoledronic acid, risedronic acid, ibandronic acid, incadronic acid, a salt therefor and/or a hydrate thereof allows the gamma delta T cells to be expanded in a culture. Purification during cell culture may also be achieved by the addition of synthetic antigens such as phosphostim/bromohalohydrin pyrophosphate (BrHPP), synthetic isopentenyl pyrophosphate (IPP), (E)-4-Hydroxy-3-methyl-but-2-enyl pyrophosphate (HMB-PP) or co-culture with artificial antigen presenting cells (aAPC) (Wang et al., 2011). The addition of such components provides a culturing environment which allows for positive selection of gamma delta T cells typically at 70% or greater by number of total cells in the purified sample. The addition of such components provides a culturing environment which allows for positive selection of gamma delta T cells typically at 70% by number of total cells in the purified sample.

An aminobisphosphonate can be added any time from the first day of culturing the gamma delta T cells. An aminobisphosphonate can be added at a concentration of 0.05 to 100 micromolar, preferably 0.1 to 30 micromolar to the peripheral blood mononuclear cells. Suitably, the bisphosphonate is an analogue of pyrophosphoric acid and is a compound in which the O (oxygen atom) of the pyrophosphoric acid skeleton P—O—P is substituted with C (carbon atom) (P—C—P). It is generally used as a therapeutic drug for osteoporosis. The aminobisphosphonate refers to a compound having N (nitrogen atom) among the bisphosphonates. For example, the aminobisphosphonate used in the present invention is not particularly limited; aminobisphosphonates and the like as disclosed in WO 2006/006720 and WO 2007/029689 may be used. Specific examples thereof include pamidronic acid, its salt and/or their hydrate, alendronic acid, its salt and/or their hydrate, and zoledronic acid, its salt and/or their hydrate. The concentration of the aminobisphosphonates is preferably 1 to 30 μM for pamidronic acid, its salt and/or their hydrate, 1 to 30 μM for alendronic acid, its salt and/or their hydrate, and 0.1 to 10 μM for zoledronic acid, its salt and/or their hydrate. Here, 5 μM zoledronic acid is added as an example.

Suitably, when the culture period is 7 days or more, a cell group comprising gamma delta T cells may be obtained with high purity; however, the culture is preferably performed for about 14 days to further increase the number of gamma delta T cells.

In embodiments, the period of culturing may be about 7 days or more. Suitably the period of culturing may be performed for about 14 days or greater to achieve high numbers of substantially purified gamma delta T cell populations. Culturing is typically performed for 14 days, after which time gamma delta T cells cease to continue exponential proliferation. However, certain embodiments provide for the extended culture and selective expansion of gamma delta T cells to greater numbers. Such embodiments include the provision of synthetic antigens to the culture (e.g. synthetic IPP, DMAPP, Br-HPP, HMB-PP), cyclic exposure to artificial or irradiated antigen presenting cells, the provision of immobilised antigens or antibodies or the use of umbilical cord blood as a starting material for cell culture.

Suitably, cells may be cultured in this environment for a period of at least 7 days to reset their cell surface receptor profile following a minimum of at least two population doublings.

Optionally, the step of culturing the gamma delta T cells may include steps for changing the gamma delta T cell surface receptor profile.

For example, the culture step may involve one or more sub-steps that reduce or eliminate one or more gamma delta T cell surface receptor type present in gamma delta T cells provided in the sample from the first subject. Such steps may be seen to "reset" or "partially reset" the receptor profile of the gamma delta T cells back to a naïve or partially naïve form. It is contemplated that such resetting enhances the gamma delta T cells' ability to treat cancer and viral infection. It is known that some T cell receptors can be induced by the presence of cancer or viruses in the subject from which the T cells are derived, and it has been found that these receptors can in some cases inhibit the responsiveness to tumour or viral infection by the T cells. Consequently, removing such receptors may increase the efficaciousness of the gamma delta T cells of the present invention.

The reduction or elimination of one or more gamma delta T cell receptor type may be achieved by the process of the present invention by culturing the gamma delta T cells derived from the first subject over a number of days in which the cell population increased in size a number of times. For example, cells may be cultured for a period of at least 7 days to reset their cell surface receptor profile following a minimum of at least two population doublings.

In cases where the gamma delta T cell surface receptor profile has been reset, cell surface receptors which were present on primary, uncultured gamma delta cells such as tumour-specific cell surface receptors B7-H1/PD-L1, B7-DC/PD-L2, PD-1 and CTLA-4 may be rendered absent or substantially reduced in number during the culture expansion period.

The culturing step may further include a step of monitoring the surface receptor profile of the gamma delta T cells in order to determine the appropriate duration of the culturing step required in order to significantly decrease or remove selected gamma delta T cell surface receptors, (for example, any one or any combination of the receptors discussed above). The process of monitoring gamma delta T cell receptors may, for example, be carried out using flow cytometric techniques, such as those outlined by Chan et al, Genes and Immunity (2014) 15, 25 to 32. Briefly, antibodies specific for immune checkpoint inhibitor receptors and/or ligands will be used to identify sub-populations of gamma delta T cells (co-stained with anti-Vgamma9 for example) expressing immune checkpoint inhibitors on their cell surface.

Additionally, or optionally, the culturing step of the present invention may include steps that induce the expression in the gamma delta T cells of gamma delta T cell surface receptor types that were not present on the surface of the uncultured gamma delta cells when extracted from the first subject, or steps that induce an increase in the amount of expression of cell surface receptor types that were present on the surface of the uncultured gamma delta cells when extracted from the first subject. This may be achieved by challenging the gamma delta T cells with an antigen derived from a cancer, bacterium, fungi, protozoa or a virus. This antigen can be added to the culture expansion media to increase efficacy, antigen-presenting potential and cytotoxicity of expanded gamma delta T cells. Suitably, antigens may be provided in various formats, including but not limited to, immobilised antigens or antibodies, irradiated tumour cell lines, artificial antigen presenting cells and addition of synthetic soluble antigens. The antigen may be added to the culture expansion media on the first day of culturing. In embodiments the virus can be selected from influenza, HIV, Hepatitis C, Hepatitis B, Herpes variants, Cytomegalovirus (CMV), Epstein Barr Virus, Chickenpox, Papillomavirus, Ebola, Varicella Zoster virus or Smallpox. Alternatively the antigen can be an antigen found in a cell infection, bacterial infection, fungal infection or protozoan infection. In particular the target antigen can be from influenza, HIV, Hepatitis C, Hepatitis B, Herpes variants, Cytomegalovirus (CMV), Ebola virus, Epstein Barr Virus, Chickenpox, Papillomavirus, Varicella Zoster virus or Smallpox.

Suitably, the antigen may include an active or inactivated viral fragment, peptide, a protein, antigenic segment or the like from such a virus organism.

Suitably, the antigen may include a tumour-specific antigen which is present only on tumour cells and not on any other cells and/or a tumour-associated antigen which is present on some tumour cells and also some normal cells. Such tumour-specific antigens may include, but are not limited to, carcinoembryonic antigen, CA-125, MUC-1, epithelial tumour antigen and a MAGE-type antigen including MAGEA1, MAGEA3, MAGEA4, MAGEA12, MAGEC2, BAGE, GAGE, XAGE1B, CTAG2, CTAG1, SSX2, or LAGE1 or combinations thereof.

Suitably, a lysate of an infected cell, a necrotic cell, or a cancer cell may be utilised to provide a suitable antigen. In embodiments the antigen may be a synthesised antigen, for example, a synthetic peptide. Alternatively, the antigen may be harvested from a subject. Suitable, around 0.02-2 micro grams per ml of antigen may be provided to the cells during the culturing step.

In embodiments, factors which encourage proliferation of gamma delta T cells and maintenance of cellular phenotype such as IL-2, IL-15 or IL-18 (Garcia V. et al., 1998, Nussbaumer O. et al., 2013) may be provided in the step of culturing the peripheral blood mononuclear cells. Suitably, in such embodiments IL-2, IL-15 or IL-18 or combinations thereof may be provided in the range of 50-2000 U/ml, more preferably 400-1000 U/ml to the culturing medium. Culture is typically performed at 34 to 38 deg. C., more preferably 37 deg. C. in the presence of 2 to 10%, more preferably 5% $CO_2$. Culture medium may be added depending on the number of cultured cells. Suitably serum may be added in an amount of 0.1 to 20% to the culture solution. As the serum, fetal calf serum AB serum, or auto-plasma may be used, for example. Suitably, a chemically defined serum replacement may be used in place of serum or plasma.

In embodiments, factors which encourage the revival of exhausted or anergic gamma delta T cells may be added to the culture medium. Suitably, these factors may include cytokines such as IL-15 or IL-18 or antibodies targeting specific immune check-point inhibitor receptors or ligands for example anti-PD-L1 antibody (Chang K. et al., 2014) but may also include antibodies directed to CTLA-4, PD-1, PD-2, LAG3, CD80, CD86, B7-H3, B7-H4, HVEM, BTLA, KIR, TIM3 or A2aR.

In embodiments, the providing step may include the collection of blood or umbilical cord blood from a donor subject. Such blood collection may be of about for example, around 15-25 ml of blood from a donor subject. In embodiments the providing step may include a collecting step wherein the step of collecting is the collection of at least gamma delta T cells from the first subject in a single collection process. In embodiments the collecting step can be over multiple collection sessions.

In embodiments of the invention the process for providing gamma delta T cells can comprise an analysing step of determining at least one characteristic of a cell collected from a first subject. In embodiments at least one characteristic of a cell can be a DNA or RNA sequence or amino acid sequence of the cell, a proteome of the cell or a cell surface marker of the cell. In embodiments the process can include a step of tissue typing the gamma delta T cells. Gamma delta cell surface marker characteristics may include (but are not limited to) CD3, CD4, CD8, CD69, CD56, CD27 CD45RA, CD45, TCR-Vg9, TCR-Vd2, TCR-Vd1, TCR-Vd3, TCR-pan g/d, NKG2D, monoclonal chemokine receptor antibodies CCR5, CCR7, CXCR3 or CXCR5 or combinations thereof. This typing may include genotypic or phenotypic information. Phenotypic information may include observable or measurable characteristics at the microscopic, cellular, or molecular level. Genotypic information may relate to specific genetic various or mutations, for example, of the human leukocyte antigen (HLA type of the donor).

Suitably the gamma delta T cells of the present invention may provide banks of clinical grade cell lines that can be expanded and differentiated for use in a large number of patients. In embodiments, gamma delta T cells may be expanded ex vivo from umbilical cord blood starting material and combined from multiple donors to generate sufficient numbers of gamma delta T cells to populate a cell bank. Such cell banks form and the isolated cells therein form separate aspects of the invention. In embodiments such a bank would suitably be populated with gamma delta T cells obtained from healthy volunteer donors of blood group O that are selected to maximize the opportunity for Human Leukocyte Antigens (HLA) matching and thereby minimise the risk of allograft rejection or need for substantial use of immunosuppressive drugs. For instance such banks for UK/EU patients may comprise the following which would allow treatment of a significant percentage of the UK/EU population with reduced risk of rejection:

| HLA-A | HLA-B | HLA-DR |
|---|---|---|
| A1 | B8 | DR17(3) |
| A2 | B44(12) | DR4 |
| A3 | B7 | DR15(2) |
| A2 | B7 | DR15(2) |
| A2 | B44(12) | DR7 |
| A2 | B62(15) | DR4 |
| A1 | B57(17) | DR7 |
| A3 | B35 | DR1 |
| A29(19) | B44(12) | DR7 |
| A2 | B60(40) | DR4 |
| A2 | B8 | DR17(3) |
| A2 | B27 | DR1 |
| A2 | B44(12) | DR13(6) |
| A3 | B7 | DR4 |
| A1 | B8 | DR4 |
| A2 | B57(17) | DR7 |
| A2 | B60(40) | DR13(6) |
| A11 | B35 | DR4 |
| A2 | B44(12) | DR11(5) |
| A24(9) | B7 | DR15(2) |
| A30(19) | B13 | DR7 |
| A31(19) | B60(40) | DR4 |
| A3 | B7 | DR1 |
| A11 | B35 | DR1 |
| A3 | B65(14) | DR13(6) |

In embodiments collected and processed gamma delta T cells of the present invention can be banked for future use at a cell bank or depository. Accordingly, the cells may be stored in a cryoprotectant such as DMSO or CryoStor™ and subjected to a controlled rate of freezing and storage with in liquid nitrogen. The gamma delta T cells may be stored in a unitised storage of defined units or dosages as required for a single or multiple treatment steps.

In an embodiment the process can comprise a step of treating a population of cells collected from a first subject with an agent to enhance the storage, viability or therapeutic ability of gamma delta T cells within the collected sample. In an embodiment, the process can include a preserving step wherein a cryopreservation agent is provided to gamma delta T cells in the sample of gamma delta T cells.

In embodiments a gamma delta T cell can be a phosphoantigen isopentenyl pyrophosphate (IPP) expanded human Vγ9Vδ2 T cell.

The predominant peripheral blood γδ T cell subset expresses a canonical Vγ9Vδ2 TCR, which recognises target cells in TCR-dependent fashion, based on dysregulation of the mevalonate pathway, via sensing enhanced levels of small molecular weight (~350 Da) pyrophosphate antigens. These can be either exogenously derived, denoting bacterial infection (such as HMBPP) or endogenous, denoting enhanced isoprenoid synthesis during tumourigenesis (IPP).

Vγ9Vδ2 cells appear to recognise a cell surface glycoprotein BTN3A1, which is expressed on an extremely wide range of target cells, containing a cytoplasmic B30.2 domain that specifically binds pyrophosphate antigens, leading to BTN3A1 clustering and productive TCR recognition. Importantly, although Vγ9Vδ2 activation is dependent on TCR signalling, mediated via CD3zeta and ZAP-70, it is strongly influenced by costimulatory pathways, which can be mediated by costimulatory receptors such as CD28, or "stress-focussed" receptors such as NKG2D, which enhance PI3-kinase pathway signals that ultimately integrate with TCR-mediated signalling.

In embodiments a gamma delta T cell can be an expanded human Vδ1 T, Vδ2 T or Vδ3 T cell.

There is also provided a method of treating an infection or cancer in an individual comprising the step of providing said individual with gamma delta T cells obtained from a different individual. Thus, donor gamma delta T cells are used for the treatment of an infection, for example, of a virus, bacteria, fungi or protozoa, or for treatment of a cancer in a recipient subject wherein the donor and the recipient are not the same individual. As will be understood, prior to providing the gamma delta T cells to the second subject, these gamma delta T cells are modified as discussed herein, to provide CAR modified gamma delta T cells.

Suitably, the method of administration to provide the gamma delta T cells to the recipient subject may include intravenous, intradermal, or subcutaneous injection. Administration may be into an affected area or systemically to the individual. Suitably the method of administration can be prophylactic, wherein a "prophylactically effective amount" or a "therapeutically effective amount" (as the case may be, although prophylaxis may be considered therapy), of the gamma delta T cells which is sufficient to show benefit to the individual, is provided. The actual amount administered, and rate and time-course of administration, will depend on the nature and severity of what is being treated. Prescription of treatment, e. g. decisions on dosage etc, is within the responsibility of general practitioners and other medical doctors.

In embodiments there is provided gamma delta T cells from a first subject for use in the treatment of a second different subject infected by a virus, bacteria fungi or protozoa wherein said treatment of the subject is allogeneic.

In embodiments there is provided gamma delta T cells from a first subject for the treatment of a second different subject infected by virus, wherein said virus is selected from HIV, influenza, or hepatitis, wherein said treatment is allogeneic. In an embodiment the virus can be hepatitis B or hepatitis C, influenza, Herpes variants, Cytomegalovirus (CMV), Epstein Barr Virus, Chickenpox, Papillomavirus, Varicella Zoster virus or Smallpox.

In embodiments the influenza virus can be influenza A (Flu A) virus. In embodiments the influenza virus can be an avian or swine-origin pandemic influenza virus, for example, H5N1, H7N3, H7N7, H7N9 and H9N2 (avian subtypes) or H1N1, H1N2, H2N1, H3N1, H3N2 H2N3 (swine subtypes).

In embodiments there is provided gamma delta T cells for the treatment of a subject with cancer wherein said treatment is allogeneic.

In embodiments there is provided gamma delta T cells from a first subject for use in the treatment of a second subject wherein the second subject is suffering from at least one of a viral, bacterial, fungal or protozoan infection. In embodiments the subject being provided with gamma delta T cells can be simultaneously, sequentially or separately administered with immunosuppressive drugs. The administration of immunosuppressive drugs can help mitigate any detrimental system response to the gamma delta T cells.

In embodiments, there is provided gamma delta T cells for the treatment of a subject with Epstein-Barr virus-induced lymphoproliferative disease (EBV-LPD).

Epstein-Barr virus (EBV) is a member of the gamma herpes virus family and is prevalent in Western populations (>90% of adults are seropositive). EBV is maintained as a latent infection by the host's cytotoxic T cells (CTLs) which prevent viral reactivation thus allowing EBV to persist asymptomatically as a latent infection in host β cells.

EBV is associated with a number of malignancies of β cell origin such as Burkitts lymphoma (BL), Hodgkins lymphoma (HL) and post-transplant lymphoproliferative disease (PTLD) in addition to cancers of epithelial origin such as nasopharynx-geal carcinoma (UPC) and gastric cancer.

PTLD is a common risk associated with solid organ transplantation and hematopoietic stem cell transplantation.

In embodiments there is provided gamma delta T cells from a first subject for use in the treatment of a second subject with an EBV-associated malignancy.

In embodiments, there is provided gamma delta T cells, in particular with Vγ9Vδ2 cells, comprising at least one co-stimulatory CAR, for use in the treatment of a subject autologously or allogeneically.

In embodiments there is provided gamma delta T cells of one or more specific gamma delta TCR isotypes for the treatment of different viral indications. For example, Vδ2$^{pos}$ subtypes may be most efficacious in the treatment of HIV and influenza infection (Wallace M. et al., 1996, Tu W. et al. 2011), whilst evidence exists for the role of at least two gamma delta T cell subtypes in the control of EBV infected cells; Vδ1$^{pos}$ (Farnault L, et al., 2013) and Vδ2$^{pos}$ cells (Xiang Z. et al., 2014). Suitably, combinations of gamma delta T cell subtypes may be chosen and administered to the patient to increase the effectiveness of the gamma delta T cell therapy. Suitably, these may comprise single isotype gamma delta T cell populations generated using discrete culturing conditions or a multivalent gamma delta T cell population generated concomitantly using a defined single set of cell culture parameters.

In embodiments there is provided gamma delta T cells, in particular Vγ9Vδ2 cells and pyrophosphate/phosphonate drugs for use in treating a subject autologously or allogeneically.

Also provided is a process for providing gamma delta T cells autologously to a subject comprising the steps
  providing a sample of gamma delta T cells from a subject;
  culturing the gamma delta T Cells to allow them to be administered back to the subject, wherein said culturing step comprises modifying the gamma delta T cells to provide CAR modified gamma delta T cells, preferably 'co-stimulatory' or 'TCR-tuneable' CAR as discussed herein.

Any of the steps of providing and culturing described above may be applied to gamma delta T cells of the present invention may be applied. For example, the step of culturing the gamma delta T cells may include steps for changing the gamma delta T cell surface receptor profile, as discussed above.

Also provided, is a method of treating an infection or cancer in an individual comprising the step of providing said individual with gamma delta T cells obtained from that individual, wherein the gamma delta T cells have been provided by a process as described by the present invention.

In embodiments the cancer can be a myeloma or melanoma. In embodiments a cancer can include but is not limited to a tumour type, including gastric cancer, renal cell carcinoma, hepatocellular carcinoma, pancreatic cancer, acute myeloid leukaemia, multiple myeloma and acute lymphoblastic leukaemia, non-small cell lung cancer, EBV-LPD, Burkitt's lymphoma and Hodgkin's disease.

According to a further aspect of the present invention, there is provided an isolated gamma delta T cell as used in the present invention, in particular a Vγ9Vδ2 cell comprising at least one co-stimulatory CAR. In embodiments there is provided an isolated gamma delta T cell, in particular a Vγ9Vδ2 cell, specifically a gamma delta T cell, for example a Vγ9Vδ2 cell comprising at least one co-stimulatory CAR and a pyrophosphate/phosphonate drug as a kit for use in combination to treat a subject autologously or allogeneically.

According to a further aspect of the present invention there is provided a pharmaceutical composition comprising a gamma delta T cell of the present invention or of any of the processes of the present invention.

In embodiments the composition comprises a unified dose of gamma delta T cells suitable to provide to an individual to provide a therapeutic effect.

In embodiments the pharmaceutical composition can include a total dose of over $25 \times 10^9$ gamma delta T cells per person.

In embodiments, there is provided a pharmaceutical composition comprising gamma delta T cells of the present invention and an antibody immunotherapy for use in the treatment of cancer.

In embodiments an antibody immunotherapy can be an immune cascade blocking agent such as PD-1, PDL-1 and/or CTLA-4 inhibitor, PD-1, PDL-1 and CTLA-4 inhibitors, for example, as being developed by Roche and Bristol Myers Squibb.

In embodiments the pharmaceutical composition can include an antibody capable of blocking CTLA-4 inhibitory signals. Blocking of CTLA-4 signals allow T lymphocytes to recognise and destroy cells. In embodiments such an antibody can be Ipilimumab (MDX-010, MDX-101).

In embodiments the antibody can inhibit Programmed death-ligand 1 (PDL-1). In embodiments such an antibody can be selected from MPDL3280A (Roche) or MDX-1105.

In embodiments the pharmaceutical composition may be combined with a cytokine, for example, IL-2 or IL-12. In embodiments the pharmaceutical composition may include interferon gamma.

In embodiments, there is provided a pharmaceutical composition comprising gamma delta T cells of the present invention and a chemotherapeutic for use in the treatment of cancer.

In embodiments, there is provided a pharmaceutical composition comprising gamma delta T cells of the present invention and a therapeutic for use in the treatment of virus.

In embodiments the pharmaceutical composition can be used as a therapeutic or a prophylactic agent for cancer or infections.

In embodiments of the invention, the gamma delta T cell can be a Vγ9Vδ2 T cell.

Suitably, in embodiments the present invention can encompass the provision of co-stimulatory CAR sequence to a T cell or T cell-like cell of defined antigen specificity, for example an NKT cell with specificity towards α-GalCer, or for example, a mucosal-associated invariant T (MAIT) cell with specificity for vitamin B-related antigens. In embodiments a CAR (classical (including a functional CD3 zeta domain) or co-stimulatory (with a non-functional/absent CD3 zeta domain)) may be provided to a γδ T-like cell, wherein the γδ T-like cell is an αβ T cell genetically engineered to express a functional gamma delta T cell receptor. Suitably, such modified cells form an aspect of the invention. In embodiments, a CAR (classical or co-stimulatory) can be provided to a γδ T-like cell, wherein the γδ T-like cell is any T cell genetically engineered to express a functional gamma delta T cell receptor. Suitably, such modified cells form an aspect of the present invention.

In embodiments, a co-stimulatory CAR (with a non-functional/absent CD3 zeta domain) can be provided to any T cell (conventional or unconventional) with a T cell receptor with defined antigen specificity. Such modified cells form aspects of the present invention. Suitably the embodiments discussed in relation to the first aspect of the invention can be applied these modified cells which are further aspects of the invention. Suitably, such modified cells may be used as discussed herein in relation to the cells of the first aspect of the invention and embodiments thereof.

Preferred features and embodiments of each aspect of the invention are as for each of the other aspects mutatis mutandis unless context demands otherwise.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness.

Reference to cited material or information contained in the text should not be understood as a concession that the material or information was part of the common general knowledge or was known in any country.

Throughout the specification, unless the context demands otherwise, the terms 'comprise' or 'include', or variations such as 'comprises' or 'comprising', 'includes' or 'including' will be understood to imply the includes of a stated integer or group of integers, but not the exclusion of any other integer or group of integers.

Embodiments of the present invention will now be described by way of example only, with reference to the accompanying figures in which:

FIG. 1. (1A) provides a diagrammatic representation of the advantages and disadvantages of a γδ T cell of the Vgamma9 subtype expressing a classical CAR. These γδ T cells will be activated by healthy cells expressing the CAR triggering antigen and thus are prone to "on-target, off tumour" toxicity (top panel). However, these cells can demonstrate increased activation against infected or cancer cells expressing the CAR-targeted antigen due to dual signalling through the CAR and γδ TCR (bottom panel). (1B) provides a diagrammatic representation of the advantages of a γδ T cell of the Vgamma9 type expressing a costimulatory CAR. The γδ T cells expressing the costimulatory CAR will be devoid of "on-target, off tumour" toxicity (due to lack of CD3zeta domain/signal 1) but will elicit increased cytotoxic activity against infected or transformed cells that express high levels of phosphoantigens (therefore providing signal 1 via the γδ TCR) and the CAR-triggering antigen.

Figure 2:
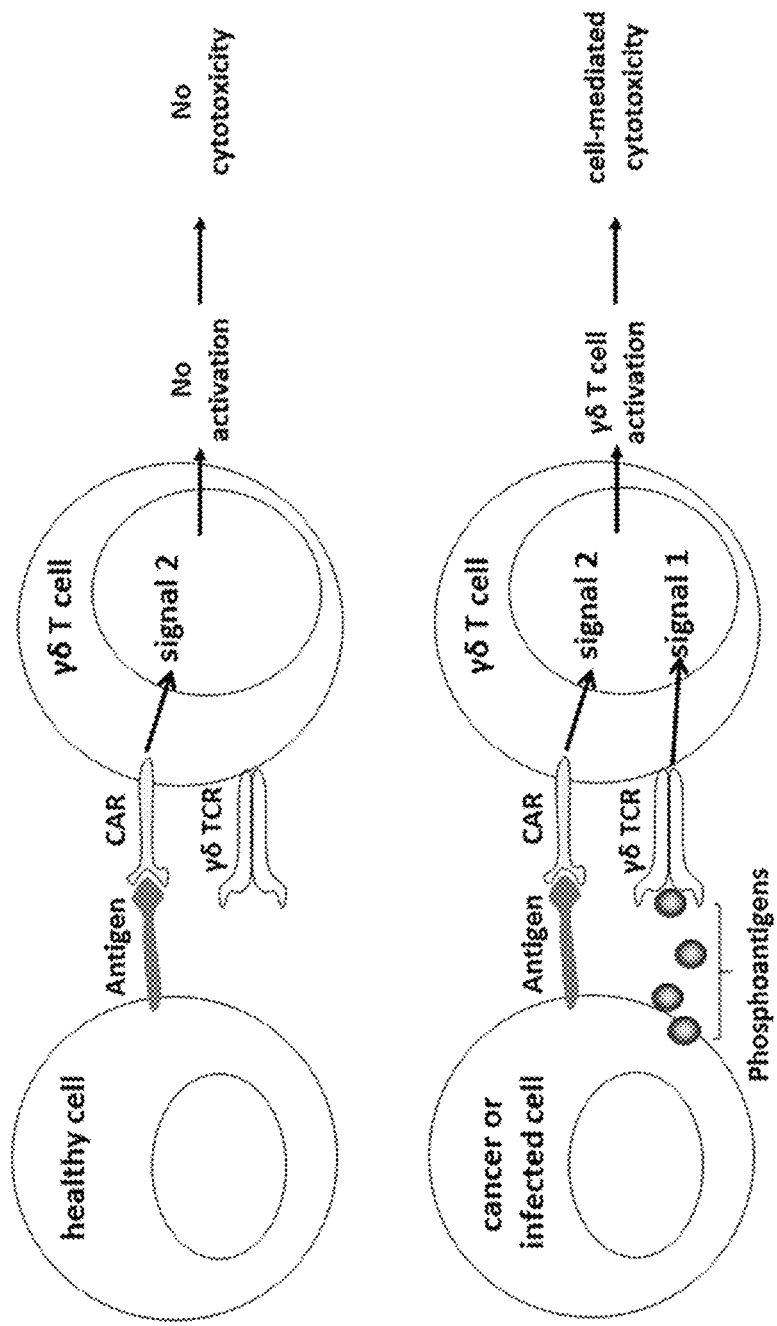

FIG. 2. provides an illustrative embodiment of the classical and costimulatory construct design. (A) A Classical-CAR construct design comprising the GMCSF-R secretion signal domain, scFv targeted against CD19, CD28 hinge, transmembrane and activation domains, CD137 (4-1BB) activation domain and CD3ζ activation domain is illustrated. (B) A co-stimulatory CAR construct comprising the GMCSF-R secretion signal domain, scFv against CD19, CD28 hinge, transmembrane and activation domains and CD137 (4-1BB) activation domain is illustrated.

Figure 3:
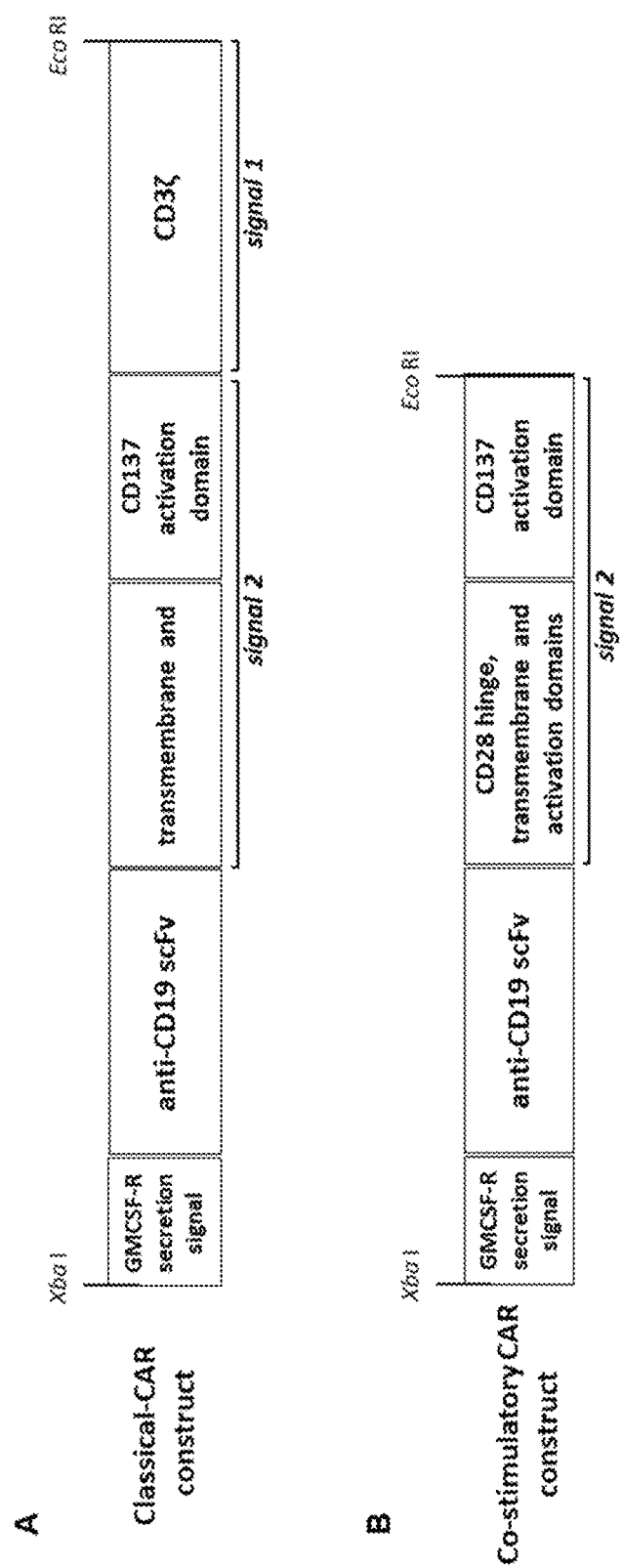

FIG. 3. provides sequences of the classical CAR construct used in the present invention. The nucleotide sequence (A) and the amino acid sequences (B) of the "classical"/"non-tuneable" CAR are provided. Each of the functional domains are annotated within the amino acid sequence, this includes the anti-CD19 scFv sequence, the CD28 hinge, transmembrane, intracellular activation domain, the CD137 (4-1BB) activation domain and the CD3ζ intracellular activation domain.

Figure 4:
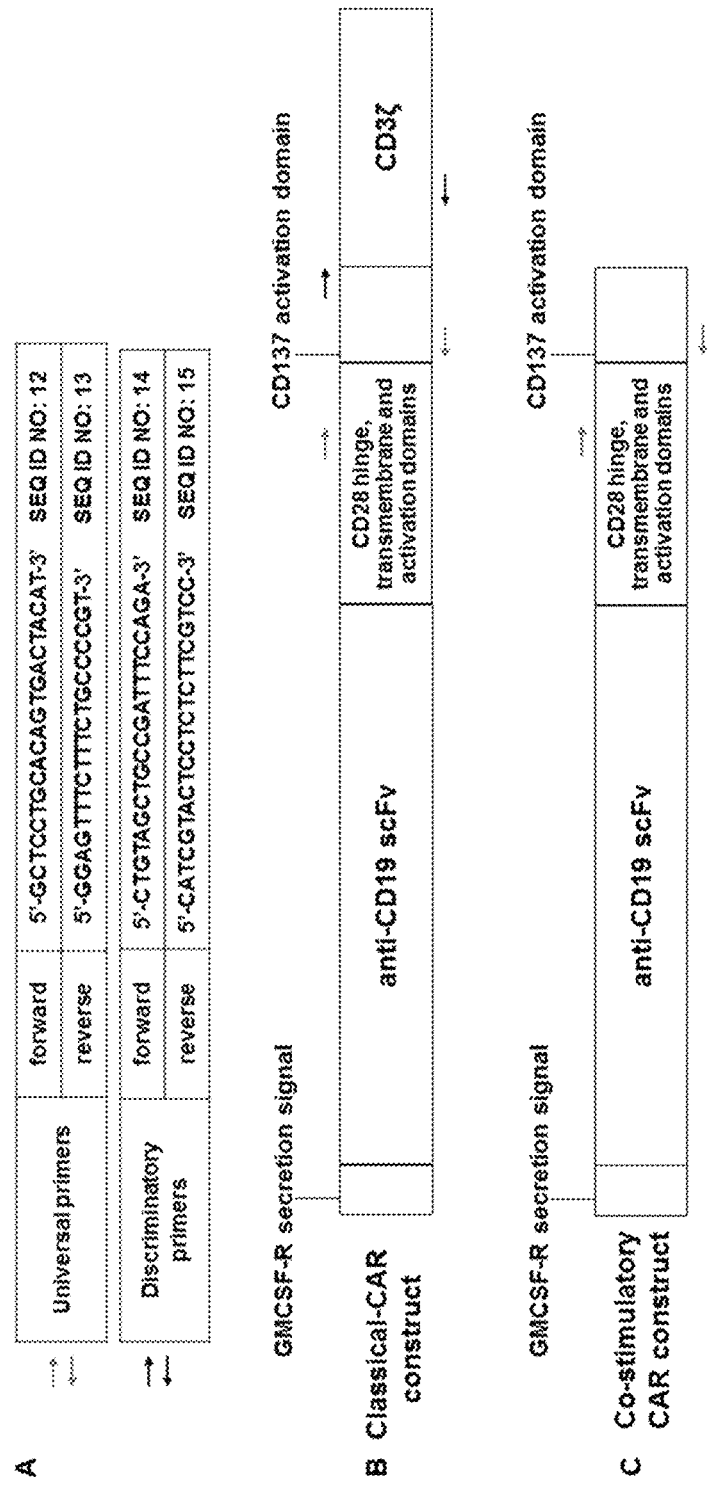

FIG. 4. provides sequences of the costimulatory CAR construct used in the present invention. The nucleotide sequence (A) and the amino acid sequences (B) of the "costimulatory"/"TCR-tuneable" CAR are provided. Each of the functional domains are annotated within the amino acid sequence, this includes the anti-CD19 scFv sequence, the CD28 hinge, transmembrane, intracellular activation domain and the CD137 (4-1BB) activation domain.

Figure 5:
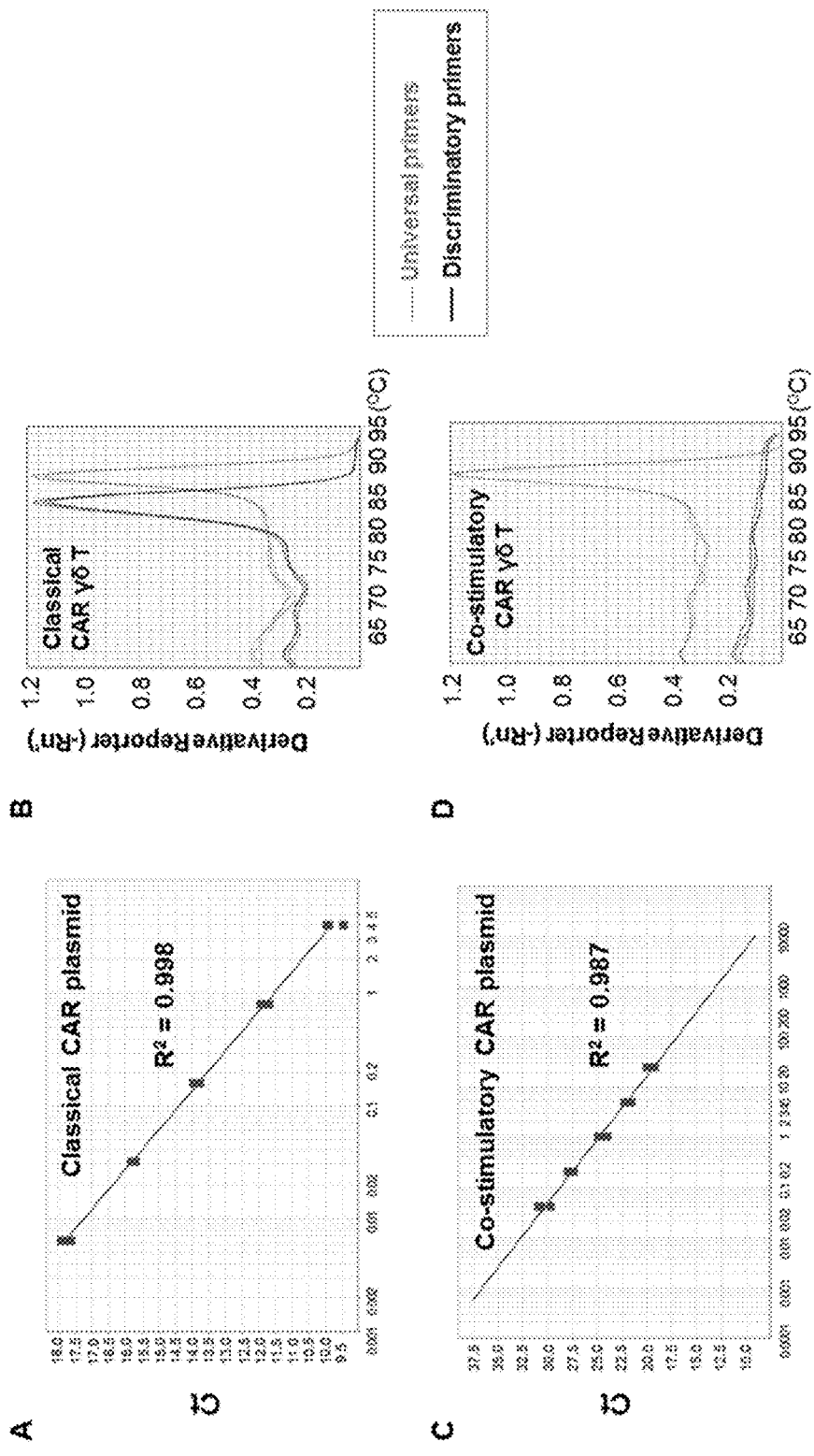

FIG. 5. illustrates a universal primer pair designed to amplify a target spanning the CD28 sequence and the CD137 (4-1BB) sequence which is present in both the classical and co-stimulatory CARs. A discriminatory primer pair was designed to generate an amplicon from sequences containing the CD137 (4-1BB) sequence and the CD3ζ activation domain, thus able to amplify product from the classical CAR but not the co-stimulatory CAR nucleotide sequence. (A) The nucleotide sequence of the two primer pairs used to detect classical CAR and co-stimulatory CAR sequence are provided. (B) Scaled illustration of the annealing locations for the universal and discriminatory primers on the classical CAR design. (C) Scaled illustration of the annealing locations for the universal primers on the co-stimulatory CAR design.

FIG. 6. illustrates qPCR amplification of serially diluted plasmid DNA using the universal primers to generate a standard curve of the classical CAR plasmid ($r^2$=0.998) (A) and the costimulatory CAR plasmid ($r^2$=0.987). (C) Thus, the universal primer pair can be used to quantitatively detect the levels of both sequences by qPCR. qPCR was performed on cells transduced with either virus. Melt curve analysis performed after 40 cycles of PCR amplification demonstrates that both primer pairs generate a single amplicon from RNA derived from the classical CAR transduced cells (B), whilst only the universal primer pair (light grey) can produce an amplicon from extracted RNA from co-stimulatory CAR transduced cells (D). This data demonstrates that both primer pairs are specific, in that they amplify only one product and that the discriminatory primer pair (dark grey) can differentiate between the two transcripts.

Figure 7:
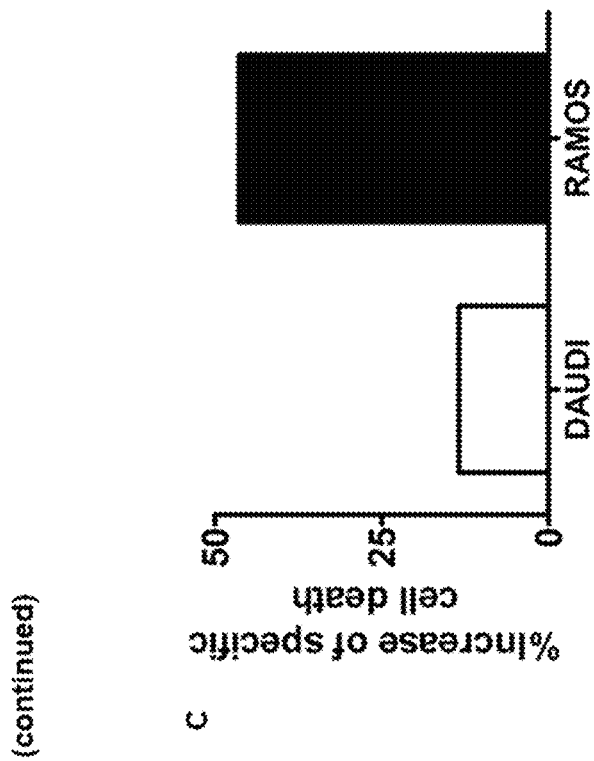

FIG. 7. Two B cell lymphoma cell lines were assessed for CD19 target antigen expression by flow cytometry; Daudi (top panel) and Ramos (bottom panel) Burkitt's lymphoma cells. 98% of the cells within each cell line expressed CD19 with the Daudi cells displaying higher intensity/expression levels as determined by MFI (A). Increased cytotoxic ability of Vgamma9 γδ T cells expressing the classical CAR construct against CD19+ cancer cell lines in comparison to non-transduced γδ T cells was observed. PBMCs were transduced with lentiviral vectors containing classical CAR sequence, 48 hrs after their stimulation with zoledronic acid. Transduced cells were expanded for a further 7 days and their cytolytic ability against the CD19 positive cell lines Daudi (top panel) and Ramos (bottom panel) was investigated by flow cytometry. The Daudi and Ramos cells were fluorescently labelled with the non-toxic cell membrane marker PKH67 which permits their detection by flow cytometry. The fluorescent target cells were co-cultured for 4.5 hours with the transduced classical-CAR (right hand side) (or non-transduced) γδ T cells (left hand side). The viability of the target cancer cell lines was assessed by Annexin V and PI staining (B). Cancer cells expressing Annexin V or Annexin V and PI were considered as early and late apoptotic respectively. Daudi cells exhibit a higher relative sensitivity to γδ T cell-mediated killing (76.4% specific cell death) and this was further increased when Daudi cells were co-cultured with classical CAR γδ T cells (86.4% specific cell death). Ramos cells were comparatively less sensitive to γδ T cell-mediated killing (39% specific cell death), however, this was markedly enhanced when the Ramos cells were co-cultured with classical CAR γδ T cells. Significantly higher levels of cytolysis were observed (55% specific cell death). This data clearly demonstrates that classical CAR expressing γδ T cells have increased cytolytic ability against CD19 positive cancer cell lines when compared to non-transduced γδ T cells. The percentage increase in specific cell death with classical-CAR γδ T cells was higher in the Ramos cell line (~46%) than in the Daudi cell line (~13%) (C). This data demonstrates that γδ T cells transduced with a classical CAR can increase the susceptibility of resistant cell lines to cytolysis.

FIG. 8. PBMCs, isolated from leukapheresis material, were initiated into culture with 5 μM zoledronic acid and 1000 IU/mL IL-2. After 48 hours in culture, cells were transduced with lentivirus containing the classical CAR construct a MOI of 10 and inclusion of 5 μg/mL polybrene to enhance viral transduction efficiency. Lentiviral transduction was repeated 24 hours later (day 3). On day 10, cells were assessed by flow cytometry for the purity of γδ T cells using anti-CD3 and anti-Vgamma9 antibodies. Consistently high purity γδ T cell populations are produced in all of the cell populations regardless of the transduced construct; non-transduced control (81% γδ T cells), classical-CAR (86% γδ T cells), costimulatory-CAR (89% γδ T cells) (A). On day 5, RNA was extracted from $1 \times 10^5$ cells, cDNA synthesised using random hexamers and reverse transcriptase and qPCR performed using SYBR green and the universal primers previously described. Relative quantification of CAR transcript expression of classical CAR mRNA and co-stimulatory CAR mRNA in transduced cells on day 5 post-transduction demonstrating that equivalent levels of CAR transcript expression are detected in the transduced cells, irrespective of construct (data was normalised to 18S ribosomal RNA levels and are expressed relative to CAR expression in a retronectin-based transduction) (B). Transduced cells were tested for their cytolytic ability against the CD19 positive cell lines Daudi and Ramos. Daudi and Ramos cells were pre-treated for 24 hours+/−5 μM zoledronic acid and then fluorescently labelled with the non-toxic cell membrane marker PKH67 which permits their detection by flow cytometry. The fluorescent target cells were co-cultured for 4.5 hours with the transduced classical-CAR, co-stimulatory-CAR (or non-transduced) γδ T cells. The viability of the target cancer cell lines was assessed by Annexin V and PI staining. Daudi cells were sensitive to γδ T cell-mediated cytolysis (36% specific cell death) and this was elevated by zoledronic acid pre-treatment (48% specific cell death). The levels of apoptosis were further enhanced when Daudi cells were co-incubated with γδ T cells expressing either the classical-CAR (64% specific cell death) or co-stimulatory CAR (54% specific cell death) (C). This demonstrates that a co-stimulatory CAR, which in isolation cannot provide both signals, can exhibit an additive effect when expressed in the context of an activated γδ T cell. To extend this observation, a less sensitive Ramos cell line was used. γδ T cells mediated a lower level of apoptosis in these cells (11% specific cell death), whilst zoledronic acid pre-treatment had no effect (10% specific cell death). However, the levels of apoptosis were markedly enhanced when the γδ T cells expressed either the classical-CAR (25% specific cell death) or co-stimulatory CAR (30% specific cell death) (D). This data provides further support to the functionality of a CD3ζ-deficient CAR (i.e. the co-stimulatory CAR) when antigen-engaged in the context of an activated γδ T cell.

EXAMPLES

Example 1

PBMCs were isolated by density centrifugation (lymphoprep) from leukapheresis material and cryopreserved. PBMCs were resuscitated and zoledronic acid (5 μM) stimulated PBMCs were cultured in the presence of IL-2 (1000 IU/mL) and 5% human AB serum in growth media. After 48 hours in culture (37° C., 5% CO$_2$, humidified atmosphere), cells were transduced with lentivirus containing a lenti-CMV-MCS-EF1a-puro construct with either a classical CAR sequence (anti-CD19 scFv-CD28-CD137-CD3ζ) or a co-stimulatory CAR sequence (anti-CD19 scFv-CD28-CD137) and 5 μg/mL polybrene at an MOI of 10. Transduction was repeated 24 hours later. CAR mRNA expression was verified by QPCR using universal primers which detected expression of both constructs at day 5. Specific expression of each construct was confirmed using a combination of the discriminatory primers and universal primers (as per FIGS. 5, 6).

Example 2

Cells were transduced with lentivirus containing classical CAR sequence and expanded as described in example 1. 7 days following transduction, cytotoxic activity was assessed by co-culturing transduced or non-transduced γδ T cells with CD19 positive target cell lines, Daudi or Ramos. Target cell lines were stained with the non-toxic membrane dye PKH67 (5 μM) for specific visualisation of the CD19 target population using flow cytometry. Following a 4.5 hour co-incubation with γδ T cells or classical-CAR expressing γδ T cells, co-cultures were stained with annexin V and propidium iodide (PI) to visualise apoptotic cells. The % specific cell death was calculated in the target cell population only. CAR-transduced γδ T cells elicited increased potency in CD19 positive target cells in comparison to non-transduced γδ T cells (FIG. 7).

Example 3

Cells were transduced with lentivirus containing classical CAR or costimulatory CAR sequence and expanded as described in example 1. The CD19 positive target cell lines Daudi and Ramos were pre-treated for 24 hours+/−5 μM zoledronic acid. Cytotoxic activity was assessed as described in example 2. PKH67-stained target cells (+/− zometa pre-treatment) were co-cultured with transduced or non-transduced γδ T cells. The co-stimulatory CAR expressing γδ T cells exhibited similar cytotoxicity towards the CD19 positive target cells as the classical-CAR expressing γδ T cells, despite the absence of the CD3ζ activation domain, signal 1 instead provided via activation through the γδ TCR by IPP sensing. Both CARs provided enhanced cytotoxicity towards γδ T cells when compared to non-transduced γδ T cells (FIG. 8).

Although the invention has been particularly shown and described with reference to particular examples, it will be understood by those skilled in the art that various changes in the form and details may be made therein without departing from the scope of the present invention.

The invention claimed is:

1. A modified γδ T cell, comprising:
   (i) a γδ T cell receptor, wherein the γδ T cell receptor provides a T cell receptor (TCR) signal upon binding; and
   (ii) at least one co-stimulatory chimeric antigen receptor (CAR) wherein the co-stimulatory chimeric antigen receptor is a synthetic receptor to recognise and target a cell surface target, connected to a transmembrane domain which traverses the cell membrane and connects to an intracellular co-stimulatory signaling region capable of providing a co-stimulatory signal, wherein the at least one co-stimulatory CAR provides the co-stimulatory signal upon binding the cell surface target, and wherein the at least one co-stimulatory CAR does not provide a TCR cell receptor signal.

2. The modified γδ T cell of claim 1, further comprising an inhibitory chimeric antigen receptor (ICAR), wherein the binding of an antigen by the ICAR inhibits the co-stimulatory signal.

3. The modified γδ T cell of claim 1, wherein the CAR is capable of binding to a cell surface target or natural ligand found in or associated with cell infection, bacterial infection, fungal infection or protozoan infection; an active or inactivated viral fragment; a peptide; a protein; an antigenic segment from a virus; a tumour-specific antigen or tumour associated antigen.

4. A pharmaceutical composition comprising a γδ T cell of claim 1.

5. The modified γδ T cell of claim 1, wherein the γδ T cell receptor is activated by a phosphoantigen.

6. The modified γδ T cell of claim 5, wherein the modified γδ T cell is of a Vγ9Vδ2 isotype.

7. The modified γδ T cell of claim 6, wherein the γδ T cell receptor is activated by isopentenyl pyrophosphate (IPP).

8. The modified γδ T cell of claim 1, wherein the at least one co-stimulatory chimeric antigen receptor comprises a non-functional CD3 zeta domain or lacks a CD3 zeta domain.

* * * * *

SEQUENCE LISTING

<160> NUMBER OF SEQ ID NOS: 15

<210> SEQ ID NO 1
<211> LENGTH: 1599
<212> TYPE: DNA
<213> ORGANISM: Artificial Sequence
<220> FEATURE:
<223> OTHER INFORMATION: Nucleic acid sequence of non-tuneable / classical CAR

<400> SEQUENCE: 1

```
atgcttctcc tggtgacaag ccttctgctc tgtgagttac cacacccagc attcctcctg      60
atcccagaca tccagatgac acagactaca tcctccctgt ctgcctctct gggagacaga     120
gtcaccatca gttgcagggc aagtcaggac attagtaaat atttaaattg gtatcagcag     180
aaaccagatg gaactgttaa actcctgatc taccatacat caagattaca ctcaggagtc     240
ccatcaaggt tcagtggcag tgggtctgga acagattatt ctctcaccat tagcaacctg     300
gagcaagaag atattgccac ttactttgc aacagggta atacgcttcc gtacacgttc       360 ggaggggggga ctaagttgga aataacaggc tccacctctg gatccggcaa gcccggatct     420
ggcgagggat ccaccaaggg cgaggtgaaa ctgcaggagt caggacctgg cctggtggcg     480
ccctcacaga gcctgtccgt cacatgcact gtctcagggg tctcattacc cgactatggt     540
gtaagctgga ttcgccagcc tccacgaaag ggtctggagt ggctgggagt aatatggggt     600
agtgaaacca catactataa ttcagctctc aaatccagac tgaccatcat caaggacaac     660
tccaagagcc aagtttttctt aaaaatgaac agtctgcaaa ctgatgacac agccatttac     720
tactgtgcca acattatta ctacggtggt agctatgcta tggactactg gggtcaagga     780
acctcagtca ccgtctcctc agcggccgca attgaagtta tgtatcctcc tccttaccta     840
gacaatgaga agagcaatgg aaccattatc catgtgaaag gaaacacct tgtccaagt     900 cccctatttc ccggaccttc taagcccttt tgggtgctgg tggtggttgg gggagtcctg     960
gcttgctata gcttgctagt aacagtggcc tttattattt tctgggtgag gagtaagagg    1020
agcaggctcc tgcacagtga ctacatgaac atgactcccc gccgccccgg gcccacccgc    1080
aagcattacc agccctatgc cccaccacgc gacttcgcag cctatcgctc caacggggc     1140 agaaagaaac tcctgtatat attcaaacaa ccatttatga gaccagtaca aactactcaa    1200
gaggaagatg gctgtagctg ccgatttcca gaagaagaag aaggaggatg tgaactgaga    1260
gtgaagttca gcaggagcgc agacgccccc gcgtaccagc agggccagaa ccagctctat    1320
```

```
aacgagctca atctaggacg aagagaggag tacgatgttt tggacaagag acgtggccgg    1380
gaccctgaga tggggggaaa gccgagaagg aagaaccctc aggaaggcct gtacaatgaa    1440
ctgcagaaag ataagatggc ggaggcctac agtgagattg ggatgaaagg cgagcgccgg    1500
aggggcaagg ggcacgatgg cctttaccag ggtctcagta cagccaccaa ggacacctac    1560
gacgcccttc acatgcaggc cctgcccccct cgctaatga                          1599
```

<210> SEQ ID NO 2
<211> LENGTH: 22
<212> TYPE: PRT
<213> ORGANISM: Artificial Sequence
<220> FEATURE:
<223> OTHER INFORMATION: Secretion Signal

<400> SEQUENCE: 2

```
Met Leu Leu Leu Val Thr Ser Leu Leu Cys Glu Leu Pro His Pro
1               5                   10                  15

Ala Phe Leu Leu Ile Pro
            20
```

<210> SEQ ID NO 3
<211> LENGTH: 248
<212> TYPE: PRT
<213> ORGANISM: Artificial Sequence
<220> FEATURE:
<223> OTHER INFORMATION: Anti-CD19 scFv

<400> SEQUENCE: 3

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
```

```
225                 230                 235                 240

Val Thr Val Ser Ser Ala Ala Ala
                245

<210> SEQ ID NO 4
<211> LENGTH: 107
<212> TYPE: PRT
<213> ORGANISM: Artificial Sequence
<220> FEATURE:
<223> OTHER INFORMATION: CD28 hinge transmembrane domain co-stimulatory
      domain

<400> SEQUENCE: 4

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

<210> SEQ ID NO 5
<211> LENGTH: 42
<212> TYPE: PRT
<213> ORGANISM: Artificial Sequence
<220> FEATURE:
<223> OTHER INFORMATION: CD137 4-1BB co-stimulatory domain

<400> SEQUENCE: 5

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 6
<211> LENGTH: 112
<212> TYPE: PRT
<213> ORGANISM: Artificial Sequence
<220> FEATURE:
<223> OTHER INFORMATION: CD3 zeta activation domain

<400> SEQUENCE: 6

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
```

```
                65                  70                  75                  80
Arg Arg Gly Lys Gly His Asp Gly Leu Tyr Gln Gly Leu Ser Thr Ala
                        85                  90                  95

Thr Lys Asp Thr Tyr Asp Ala Leu His Met Gln Ala Leu Pro Pro Arg
                100                 105                 110
```

<210> SEQ ID NO 7
<211> LENGTH: 1263
<212> TYPE: DNA
<213> ORGANISM: Artificial Sequence
<220> FEATURE:
<223> OTHER INFORMATION: Nucleic acid sequence of TCR-tuneable / co-stimulatory CAR

<400> SEQUENCE: 7

```
atgcttctcc tggtgacaag ccttctgctc tgtgagttac cacacccagc attcctcctg     60
atcccagaca tccagatgac acagactaca tcctccctgt ctgcctctct gggagacaga    120
gtcaccatca gttgcagggc aagtcaggac attagtaaat atttaaattg gtatcagcag    180
aaaccagatg gaactgttaa actcctgatc taccatacat caagattaca ctcaggagtc    240
ccatcaaggt tcagtggcag tgggtctgga acagattatt ctctcaccat tagcaacctg    300
gagcaagaag atattgccac ttacttttgc caacagggta atacgcttcc gtacacgttc    360
ggaggggga  ctaagttgga aataacaggc tccacctctg gatccggcaa gcccggatct    420
ggcgagggat ccaccaaggg cgaggtgaaa ctgcaggagt caggacctgg cctggtggcg    480
ccctcacaga gcctgtccgt cacatgcact gtctcagggg tctcattacc cgactatggt    540
gtaagctgga ttcgccagcc tccacgaaag ggtctggagt ggctgggagt aatatggggt    600
agtgaaacca catactataa ttcagctctc aaatccagac tgaccatcat caaggacaac    660
tccaagagcc aagttttctt aaaaatgaac agtctgcaaa ctgatgacac agccatttac    720
tactgtgcca acattatta  ctacggtggt agctatgcta tggactactg ggtcaagga    780
acctcagtca ccgtctcctc agcggccgca attgaagtta tgtatcctcc tccttaccta    840
gacaatgaga gagcaatgg  aaccattatc catgtgaaag ggaaacacct ttgtccaagt    900
cccctatttc ccggaccttc taagccctt  tgggtgctgg tggtggttgg gggagtcctg    960
gcttgctata gcttgctagt aacagtggcc tttattattt tctgggtgag gagtaagagg   1020
agcaggctcc tgcacagtga ctacatgaac atgactcccc gccgcccgg  gcccaccgc   1080
aagcattacc agccctatgc cccaccacgc gacttcgcag cctatcgctc caacgggggc   1140
agaaagaaac tcctgtatat attcaaacaa ccatttatga ccagtacaa  actactcaa   1200
gaggaagatg gctgtagctg ccgatttcca gaagaagaag aaggaggatg tgaactgtaa   1260
tga                                                                  1263
```

<210> SEQ ID NO 8
<211> LENGTH: 22
<212> TYPE: PRT
<213> ORGANISM: Artificial Sequence
<220> FEATURE:
<223> OTHER INFORMATION: Secretion signal

<400> SEQUENCE: 8

```
Met Leu Leu Leu Val Thr Ser Leu Leu Leu Cys Glu Leu Pro His Pro
1               5                   10                  15

Ala Phe Leu Leu Ile Pro
            20
```

<210> SEQ ID NO 9
<211> LENGTH: 248
<212> TYPE: PRT
<213> ORGANISM: Artificial Sequence
<220> FEATURE:
<223> OTHER INFORMATION: Anti-CD19 scFv

<400> SEQUENCE: 9

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Ala Ala Ala
                245
```

<210> SEQ ID NO 10
<211> LENGTH: 107
<212> TYPE: PRT
<213> ORGANISM: Artificial Sequence
<220> FEATURE:
<223> OTHER INFORMATION: CD28 hinge transmembrane domain co-stimulatory
    domain

<400> SEQUENCE: 10

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
```

```
                    50                  55                  60
Trp Val Arg Ser Lys Arg Ser Arg Leu Leu His Ser Asp Tyr Met Asn
 65                  70                  75                  80

Met Thr Pro Arg Arg Pro Gly Pro Thr Arg Lys His Tyr Gln Pro Tyr
                 85                  90                  95

Ala Pro Pro Arg Asp Phe Ala Ala Tyr Arg Ser
            100                 105
```

<210> SEQ ID NO 11
<211> LENGTH: 42
<212> TYPE: PRT
<213> ORGANISM: Artificial Sequence
<220> FEATURE:
<223> OTHER INFORMATION: CD137 4-1BB co-stimulatory domain

<400> SEQUENCE: 11

```
Lys Arg Gly Arg Lys Lys Leu Leu Tyr Ile Phe Lys Gln Pro Phe Met
  1               5                  10                  15

Arg Pro Val Gln Thr Thr Gln Glu Glu Asp Gly Cys Ser Cys Arg Phe
             20                  25                  30

Pro Glu Glu Glu Glu Gly Gly Cys Glu Leu
         35                  40
```

<210> SEQ ID NO 12
<211> LENGTH: 21
<212> TYPE: DNA
<213> ORGANISM: Artificial Sequence
<220> FEATURE:
<223> OTHER INFORMATION: Universal primer - forward

<400> SEQUENCE: 12
gctcctgcac agtgactaca t                                           21

<210> SEQ ID NO 13
<211> LENGTH: 20
<212> TYPE: DNA
<213> ORGANISM: Artificial Sequence
<220> FEATURE:
<223> OTHER INFORMATION: Universal primer - reverse

<400> SEQUENCE: 13
ggagtttctt tctgccccgt                                             20

<210> SEQ ID NO 14
<211> LENGTH: 21
<212> TYPE: DNA
<213> ORGANISM: Artificial Sequence
<220> FEATURE:
<223> OTHER INFORMATION: Discriminatory primer - forward

<400> SEQUENCE: 14
ctgtagctgc cgatttccag a                                           21

<210> SEQ ID NO 15
<211> LENGTH: 22
<212> TYPE: DNA
<213> ORGANISM: Artificial Sequence
<220> FEATURE:
<223> OTHER INFORMATION: Discriminatory primer - reverse

<400> SEQUENCE: 15
catcgtactc ctctcttcgt cc                                          22